(12) United States Patent
Min et al.

(10) Patent No.: US 10,351,904 B2
(45) Date of Patent: *Jul. 16, 2019

(54) COMPOSITION FOR DETECTING NUCLEIC ACID AND METHOD FOR DETECTING NUCLEIC ACID USING SAME

(71) Applicant: SNU R&DB Foundation, Seoul (KR)

(72) Inventors: Dal-Hee Min, Seoul (KR); Jieon Lee, Seoul (KR); Soo-Ryoon Ryoo, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 871 days.

This patent is subject to a terminal disclaimer.

(21) Appl. No.: 14/397,015

(22) PCT Filed: Apr. 24, 2013

(86) PCT No.: PCT/KR2013/003503
§ 371 (c)(1),
(2) Date: Oct. 24, 2014

(87) PCT Pub. No.: WO2013/162276
PCT Pub. Date: Oct. 31, 2013

(65) Prior Publication Data
US 2015/0080251 A1    Mar. 19, 2015

(30) Foreign Application Priority Data
Apr. 24, 2012  (KR) .......................... 10-2012-042785

(51) Int. Cl.
*C12Q 1/6841*  (2018.01)
*C12Q 1/6876*  (2018.01)
*C12Q 1/6823*  (2018.01)

(52) U.S. Cl.
CPC ......... *C12Q 1/6841* (2013.01); *C12Q 1/6823* (2013.01); *C12Q 1/6876* (2013.01); *C12Q 2600/178* (2013.01)

(58) Field of Classification Search
None
See application file for complete search history.

(56) References Cited

U.S. PATENT DOCUMENTS

2010/0248980 A1* 9/2010 Park et al. ........... C12Q 1/6837
506/9

FOREIGN PATENT DOCUMENTS

KR    10-2011-0120749 A    11/2011

OTHER PUBLICATIONS

He et al., "A Graphene Nanoprobe for Rapid, Sensitive, and Multicolor Fluorescent DNA Analysis," Adv. Funct. Mater. 2010, 20:453-459.*
Int'l. Search report of PCT/KR2013/003503 dated Jul. 4, 2013.
(Continued)

*Primary Examiner* — Kaijiang Zhang
(74) *Attorney, Agent, or Firm* — The PL Law Group, PLLC

(57) ABSTRACT

The present invention relates a composition, including an RNA probe which contains a fluorescence material absorbed in graphene oxide, for detecting a nucleic acid, and to a method for detecting a nucleic acid using the composition. By means of the composition and the method, the presence and expression pattern of a target nucleic acid in a sample or a cell can be observed in real time, and a plurality of target nucleic acids can be detected in multitude.

11 Claims, 29 Drawing Sheets
Specification includes a Sequence Listing.

(56) References Cited

OTHER PUBLICATIONS

Guo-Jun Zhang et al., "Label-free direct detection of MiRNAs with silicon nanowire biosensors", Biosens. Bioelectron., vol. 24, No. 8, pp. 2504-2508 (Apr. 15, 2009).

Liang Cui et al., "Graphene oxide-protected DNA probes for multiplex microRNA analysis in complex biological samples based on a cyclic enzymatic amplification method", Chemical Communications, vol. 48, No. 2. pp. 194-196 (Jan. 7, 2012)

Ying Wang et al., "Aptamer/Graphene Molecular Oxide Nanocomplex for in Situ Molecular Probing in Living Cells", J. Am. Chem. Soc., vol. 132, No. 27, pp. 9274-9276 (Jul. 14, 2010).

Zhang GJ, "Silicon nanowire biosensor for ultrasensitive and label-free direct detection of miRNAs", Methods in Molecular Biology, vol. 676, pp. 111-121 (2011).

Haifeng Dong et al., "Highly sensitive multiple microRNA detectioi based on fluorescence quenching of graphene oxide and isothermal stranddisplacement polymerase reaction", Analytical Chemistry, vol. 84, pp. 4587-4593 (Apr. 17, 2012).

Rong Hu et al., "Nucleic acid-functionalized nanomaterials for bioimaging applications", Journal of Materials Chemistry, vol. 48, No. 2, pp. 194-196 (2011).

Shiping Song et al., "Functional nanoprobes for ultrasensitive detection of biomolecules", Chemical Society Reviews, vol. 39, No. 11, pp. 4234-4243 (2010).

* cited by examiner

| | Carbon | Hydrogen | Oxygen |
|---|---|---|---|
| Composition (%) | 49.72 | 1.76 | 39.61 |

| Sample | Zeta Potential (mV) | Hydrodynamic diameter (nm) |
|---|---|---|
| Graphene Oxide | 0.308 | 223.9 |

SEQUENCE LISTING

<160> NUMBER OF SEQ ID NOS: 10

<210> SEQ ID NO 1
<211> LENGTH: 22
<212> TYPE: RNA
<213> ORGANISM: Homo sapiens

<400> SEQUENCE: 1
uagcuuauca gacugauguu ga                                    22

<210> SEQ ID NO 2
<211> LENGTH: 22
<212> TYPE: RNA
<213> ORGANISM: Homo sapiens

-continued

```
<400> SEQUENCE: 2
ucccugagac ccuaacuugu ga                                              22

<210> SEQ ID NO 3
<211> LENGTH: 23
<212> TYPE: RNA
<213> ORGANISM: Homo sapiens

<400> SEQUENCE: 3
uuaaugcuaa ucgugauagg ggu                                             23

<210> SEQ ID NO 4
<211> LENGTH: 21
<212> TYPE: RNA
<213> ORGANISM: Unknown
<220> FEATURE:
<223> OTHER INFORMATION: Base Sequence of miRNA of Plant

<400> SEQUENCE: 4
uuuggauuga agggagcucu a                                               21

<210> SEQ ID NO 5
<211> LENGTH: 22
<212> TYPE: RNA
<213> ORGANISM: Homo sapiens

<400> SEQUENCE: 5
uagcaccauc ugaaaucggu ua                                              22

<210> SEQ ID NO 6
<211> LENGTH: 22
<212> TYPE: DNA
<213> ORGANISM: Artificial Sequence
<220> FEATURE:
<223> OTHER INFORMATION: PNA probe for miRNA21

<400> SEQUENCE: 6
tcaacatcag tctgataagc ta                                              22

<210> SEQ ID NO 7
<211> LENGTH: 22
<212> TYPE: DNA
<213> ORGANISM: Artificial Sequence
<220> FEATURE:
<223> OTHER INFORMATION: PNA probe for miRNA-125b

<400> SEQUENCE: 7
tcacaagtta gggtctcagg ga                                              22

<210> SEQ ID NO 8
<211> LENGTH: 18
<212> TYPE: DNA
<213> ORGANISM: Artificial Sequence
<220> FEATURE:
<223> OTHER INFORMATION: PNA proble for miRNA-155

<400> SEQUENCE: 8
ctatcacgat tagcatta                                                   18

<210> SEQ ID NO 9
<211> LENGTH: 21
<212> TYPE: DNA
<213> ORGANISM: Artificial Sequence
<220> FEATURE:
<223> OTHER INFORMATION: PNA probe for miRNA-159
```

```
<400> SEQUENCE: 9
tagagctccc ttcaatccaa a                                          21

<210> SEQ ID NO 10
<211> LENGTH: 22
<212> TYPE: DNA
<213> ORGANISM: Artificial Sequence
<220> FEATURE:
<223> OTHER INFORMATION: PNA probe for miRNA-29a

<400> SEQUENCE: 10
taaccgattt cagatggtgc ta                                         22
```

COMPOSITION FOR DETECTING NUCLEIC ACID AND METHOD FOR DETECTING NUCLEIC ACID USING SAME

CROSS-REFERENCE TO RELATED APPLICATION

This application is a U.S. national phase application under 35 U.S.C. § 371 of International Application No. PCT/KR2013/003503 filed on Apr. 24, 2013, claiming the priority based on Korean Patent Application No. 10-2012-0042785 filed on Apr. 24, 2012, the entire disclosures of which are incorporated herein by reference.

TECHNICAL FIELD

The embodiments described herein pertain generally to a composition, which includes a PNA probe containing a fluorescent material and adsorbed on graphene oxide, for detecting a nucleic acid, and also pertain to a method of detecting a nucleic acid using the composition.

BACKGROUND

Graphene has a plane monolayer structure including a 2-dimensional lattice made of carbon atoms. Graphene is a basic structural element of various allotropes of graphite having different dimensional structures. That is, the graphene may be a basic structure of fullerene (0-dimensional structure), carbon nanotube (1-dimensional structure) or graphite stacked in a 3-dimensional structure. In many of recent researches, peculiar properties of graphene, such as a zero band gap, derived from its hexagonal crystalline structure, two interpenetrating triangular subordinate lattice structures and its one-atom-size thickness are attracting attention. Further, graphene also has a peculiar electron transmission property, and, thus, it exhibits very special phenomena which have not been conventionally observed. A half-integer quantum Hall effect and a bipolar super-current transistor effect are examples of such peculiar phenomena, and these effects are also deemed to be resulted from the unique structure of graphene. Graphene oxide (GO), which is an oxidized form of graphene, is capable of quenching a fluorescence signal of organic fluorescent pigments through FRET (Fluorescence Resonance Energy Transfer).

A method of detecting a specific nucleic acid (DNA or RNA) or protein is basically an important technique in the field of scientific research. As it becomes possible to detect and investigate a specific nucleic acid or protein, researchers can specify which genetic and biological marker is an index indicating human health condition. By using such a method of detecting a nucleic acid and a protein, gene variation of pathogen present in a sample or a specific gene expression can be observed. Further, miRNA (microRNA), which is a microscopic RNA molecule composed of about twenty (20) nucleic acids and which does not encode protein is one of important biomolecules that exist within a human body, is known to be related to various biological processes such as cell proliferation or differentiation.

PNA (Peptide Nucleic Acid) is an artificially synthesized nucleic acid. Since a backbone of oligonucleic acid is composed of peptide bonds, not phosphodiester bonds, PNA is electrically neutral while having a very strong binding force and is very stable against nuclease and proteinase. Thus, when used as a probe, PNA exhibits very high stability.

Recently, a molecular biological method or biochemical method in biology is widely employed to conduct a research on miRNA. Microarray or real-time PCR as a non-array technique are examples of the most well-known existing research methods, and various other methods are also being developed. For example, there has been reported a relevant research entitled "Bio-imaging probe for detecting intracellular molecules and treating disorders" (Korean Patent Publication No. 2011-0120749). However, these methods have drawbacks in that multiplexed-detection is impossible, a real-time detection is difficult and cost of detection is high.

DISCLOSURE OF THE INVENTION

Problems to be Solved by the Invention

In view of the foregoing problems, example embodiments provide a composition, which includes a PNA probe containing a fluorescent material and adsorbed on graphene oxide, for enabling a multiplexed-detection and real-time detection of a target nucleic acid by using properties of the graphene oxide, and also provide a method for detecting the nucleic acid by using the composition.

However, the problems sought to be solved by the present disclosure are not limited to the above description and other problems can be clearly understood by those skilled in the art from the following description.

Means for Solving the Problems

In one aspect of example embodiments, there is provided a composition for detecting a nucleic acid, including: a PNA probe adsorbed on a graphene oxide and containing a fluorescent material; wherein the nucleic acid as a target material is combined with the PNA probe so that the PNA probe is separated from the graphene oxide and a fluorescent light is emitted from the fluorescent material.

In another aspect of example embodiments, there is provided a method of detecting a nucleic acid, including: a step of mixing a composition for detecting a nucleic acid with a sample including a nucleic acid as a target material, wherein the composition includes a PNA probe adsorbed on a graphene oxide and containing a fluorescent material; and a step of detecting a fluorescent light emitted from the fluorescent material, wherein the nucleic acid as a target material is combined with the PNA probe so that the PNA probe is separated from the graphene oxide and the fluorescent light is emitted from the fluorescent material.

Effect of the Invention

By using the composition for detecting a nucleic acid and the method for detecting a nucleic acid using the composition in accordance with the example embodiments, presence or absence of a target nucleic acid in a sample or cell and an expression pattern of the target nucleic acid can be observed in a real time as well as a multiplexed-detection of plural target nucleic acids is enabled. Further, candidates of medicinal substances and low-molecular substances capable of adjusting expression of a specific miRNA positively or negatively can be derived by performing high-throughput screening (HTS). Further, a mechanism of action of the substances derived through this process and an influence of such substances upon the control of the miRNA expression can be investigated in a cell level. Additionally, since an expression pattern of a target nucleic acid within a living cell can be observed, it is possible to derive highly reliable candidates for the low-molecular substances and medicinal substances.

The composition for detecting a nucleic acid and the method of detecting a nucleic acid using the composition in accordance with the example embodiments is cost-effective because they employs graphene oxide, which is a low-price material that can be secured in large quantity and stored stably at a room temperature. Further, since a nucleic acid used as a probe is a PNA, which is stable against nuclease, a detection reaction may occur stably. In addition, since the detection is performed based on fluorescence, it is possible to read signals quantitatively, and an existing fluorescence leader or a fluorescence microscope can be utilized.

MODE FOR CARRYING OUT THE INVENTION

Figure 1:
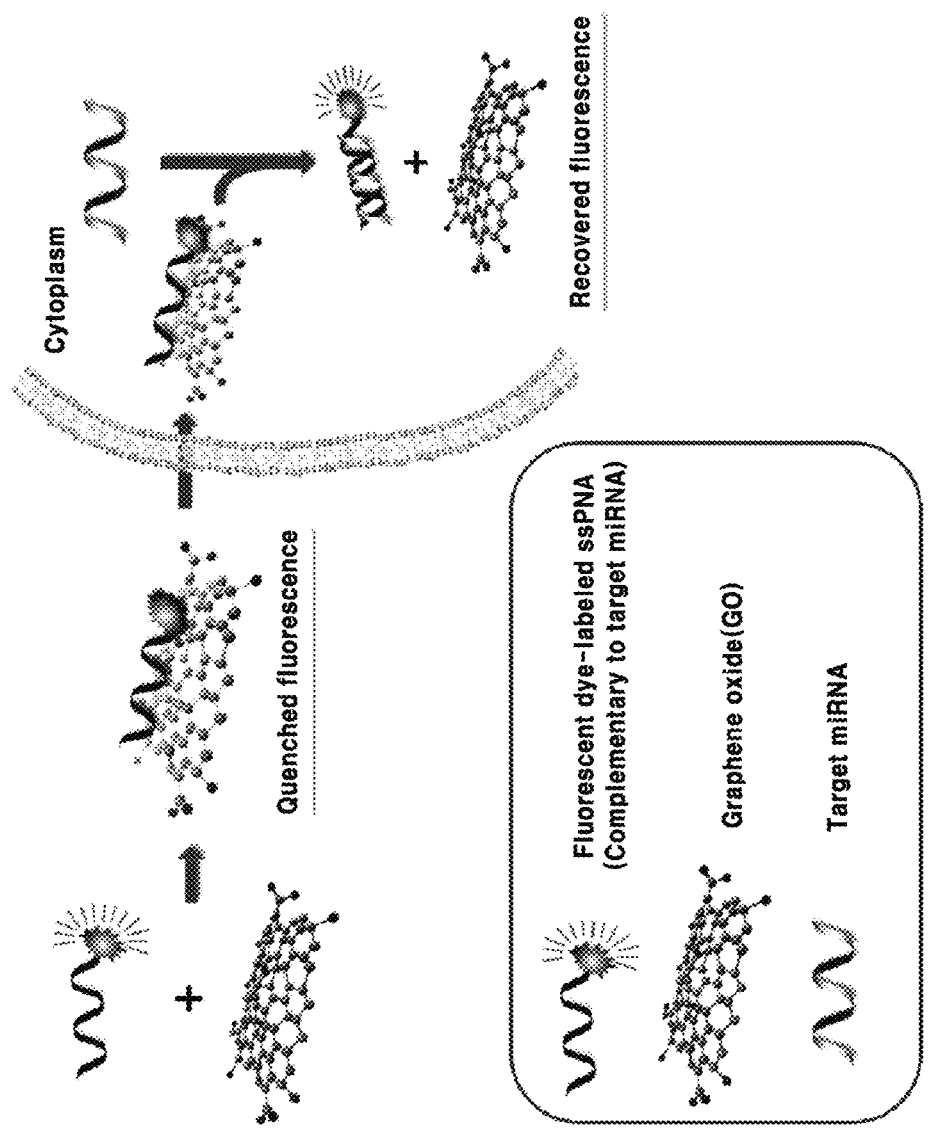
FIG. 1 is a schematic diagram illustrating a method of detecting a nucleic acid in accordance with an example embodiment of the present disclosure.

Hereinafter, example embodiments will be described in detail so that inventive concept may be readily implemented by those skilled in the art. However, it is to be noted that the present disclosure is not limited to the example embodiments and examples but can be realized in various other ways. In drawings, parts not directly relevant to the description are omitted to enhance the clarity of the drawings, and like reference numerals denote like parts through the whole document.

Through the whole document, the term "comprises or includes" and/or "comprising or including" used in the document means that one or more other components, steps, operation and/or existence or addition of elements are not excluded in addition to the described components, steps, operation and/or elements unless context dictates otherwise.

The term "about or approximately" or "substantially" are intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "on" that is used to designate a position of one element with respect to another element includes both a case that the one element is adjacent to the another element and a case that any other element exists between these two elements.

Through the whole document, the term "combinations or" included in Markush type description means mixture or combination of one or more components, steps, operations and/or elements selected from the group consisting of components, steps, operation and/or elements described in Markush type and thereby means that the disclosure includes one or more components, steps, operations and/or elements selected from the Markush group.

Through the whole document, the expression "A and/or B" means "A or B, or A and B."

Hereinafter, various example embodiments and examples will be described in detail with reference to the accompanying drawings.

In accordance with a first aspect of the present disclosure, there is provided a composition for detecting a nucleic acid, including: a PNA probe adsorbed on a graphene oxide and containing a fluorescent material; wherein the nucleic acid as a target material is combined with the PNA probe so that the PNA probe is separated from the graphene oxide and a fluorescent light is emitted from the fluorescent material.

Since a nanosized graphene oxide (nGO) is not harmful to cells, it has biocompatibility and can be introduced into cells through chemical functionalization. Further, the nGO is suitable for signal detection. Various aromatic molecules and bio-materials can be adsorbed to a hydrophobic portion on the surface of the graphene oxide, but not limited thereto. Especially, in case of oligonucleic acid, when oligonucleic acid exists in the form of a single strand, an exposed hydrophobic base of the oligonucleic acid can be adsorbed to the surface of the graphene oxide through pi-pi interaction. When oligonucleic acid exists in the form of double strands, however, the hydrophobic base would not be exposed to the outside due to hydrogen bonds between the two strands of oligonucleic acid and, thus, would not be adsorbed to the surface of the graphene oxide. By way of example, if a cell is treated with a single-strand nucleic acid probe, which has a complementary sequence to that of a DNA, a RNA or a miRNA having a specific sequence among biomolecular matters and which is adsorbed on graphene oxide, the nucleic acid probes may be combined with a target material, i.e., a DNA, a RNA or a miRNA within the cell in the form of double strands. Accordingly, the nucleic acid may not maintain adsorption to the surface of the graphene oxide and may be separated therefrom.

In accordance with an example embodiment, PNA (Peptide Nucleic Acid) may be used as the oligonucleic acid to be adsorbed to the graphene oxide, but not limited thereto. By way of example, the PNA may be a single-strand PNA and can be easily adsorbed to the surface of the graphene oxide, but not limited thereto. As for the PNA, since a backbone of oligonucleic acid is composed of peptide bonds, PNA is electrically neutral. Accordingly, the PNA has higher adsorbability to hydrophobic graphene oxide than a DNA or RNA which is electrically negative. Further, a PNA-RNA bond is stronger than a DNA-RNA bond or a RNA-RNA bond, and a Tm value of the PNA-RNA bond is higher about 1° C. per a base. Accordingly, a PNA probe has a higher binding force to nucleic acid as a target material than a DNA probe or a RNA probe. Further, since the PNA is very stable against nuclease and protease that exist within a human body, the probability of degradation of the PNA probe is much lower than that of a DNA probe, a RNA probe and a protein probe, when introduced into a cell. Additionally, since the PNA is composed of structurally strong covalent bond, the stability of the PNA can be maintained in a wide pH range under various temperature conditions. Thus, as oligonucleic acid to be used as a probe, the PNA has advantages as compared to other kinds of oligonucleic acids.

A FRET (Fluorescence Resonance Energy Transfer) phenomenon occurs between graphene oxide and organic fluorescent pigments used in accordance with an example embodiment. That is, the graphene oxide, which is an oxidized form of graphene, is capable of quenching a fluorescence signal of adjacent organic fluorescent pigments through FRET. Accordingly, if a PNA probe containing a fluorescent material is adsorbed to the graphene oxide, the fluorescent light of the fluorescent material is quenched. If, however, the PNA probe is hybridized with a DNA, a RNA or a miRNA as a target material and forms double strands, the PNA probe may not be adsorbed to the graphene oxide and separated therefrom. As a result, the fluorescent material contained in the PNA probe would not be subjected to FRET but emit fluorescent light. By measuring the fluorescent light of the sample in this process, the target material in the sample can be detected in real time and can be quantified.

For example, a bond between the nucleic acid as the target material and the PNA probe may be hybridized because the base sequence of the nucleic acid and the base sequence of the PNA probe are complementary, but not limited thereto. By way of example, the base sequence of the PNA probe may have a sequence complementary to a part or the whole of the base sequence of the nucleic acid, but not limited thereto. For example, the PNA probe may have the same length as that of the nucleic acid as the target material and may have a sequence complementary to a part or the whole of the base sequence of the nucleic acid, but not limited thereto. In accordance with an example embodiment, the PNA probe may have a length shorter than that of the nucleic acid as the target material and may have a sequence complementary to a part or the whole of the base sequence of the nucleic acid, but not limited thereto. In accordance with another example embodiment, the PNA probe may have a length longer than that of the nucleic acid as the target material and may have a sequence complementary to a part or the whole of the base sequence of the nucleic acid, but not limited thereto. For example, the complementarity between the base sequence of the PNA probe and the base sequence of the nucleic acid as the target material may be about 70%, about 80%, about 90%, about 95% or about 100%, but not limited thereto. For instance, in case that the nucleic acid as the target material is miRNA, a PNA probe having a complementary sequence to that of the miRNA may include about twenty two (22) bases, but not limited thereto. By way of example, the PNA probe may include one prepared to have a fixed sequence for commercial sales, one prepared to have a sequence designed by a purchaser, or one prepared for noncommercial purposes, but not limited thereto. By way of example, the PNA probe may include one purchased from PANAGENE Inc., but not limited thereto. For example, the PNA probe may include one combined with mature miRNA, but not limited thereto. For instance, the PNA probe may include one combined with miRNA and induces RNA interference to thereby suppress expression or functioning of the miRNA, but not limited thereto.

By way of example, the fluorescent material contained in the PNA probe may be coupled to one end of the PNA probe, or coupled to an inside within the sequence of the PNA probe, but not limited thereto. For example, the fluorescent material contained in the PNA probe may be coupled to a 5'-end or a 3'-end of the PNA probe through covalent bond, and the covalent bond may be forged between the fluorescent material and a linker connected to the 5'-end or 3'end of the PNA probe, but not limited thereto. By way of example, the covalent bond may be forged between an amino group of the linker and the fluorescent material, and the linker may be an ethylene glycol linker, but not limited thereto. By way of more specific example, the linker may be an AEEA linker or an O-linker of PANAGENE Inc., but not limited thereto. For example, the AEEA linker may have a length of about 1.3 nm and include about nine (9) atoms, but not limited thereto.

For example, the fluorescent material contained in the PNA probe may be a fluorescent material that can be applied to a living cell and can measure fluorescent light, but not limited thereto. By way of example, the fluorescent material may be selected from the group consisting of rhodamine and its derivatives, fluorescein and its derivatives, coumarin and its derivatives, acridine and its derivatives, pyrene and its derivatives, erythrosine and its derivatives, eosin and its derivatives, 4-acetamido-4'-isothiocyanatostilbene-2,2'-disulfonic acid, Cy5, Cy3, and combinations thereof, but not limited thereto.

In accordance with an example embodiment, the nucleic acid may include a DNA or RNA, but not limited thereto. By way of example, if the PNA probe containing the fluorescent material is adsorbed on the graphene oxide and introduced into a sample in which a DNA or RNA as a target material exists in the sample, the RNA probe having a complementary sequence to that of the DNA or RNA may be hybridized with the DNA or RNA and turn into a double-stranded nucleic acid. As a result, the PNA probe would be separated from the graphene oxide and the fluorescent material contained in the PNA probe emits fluorescent light without being subjected to FRET (Fluorescence Resonance Energy Transfer). Thus, by measuring the fluorescent light, the DNA or RNA existing in the sample can be detected but not limited thereto. For example, the DNA may include a DNA that encodes protein or a DNA that does not encode protein, but not limited thereto. By way of example, the RNA may include mRNA (messenger RNA), a tRNA (transfer RNA), a rRNA (ribosomal RNA), a s RNA (small RNA), a snRNA (small nuclear RNA), a scRNA (small cytoplasmic RNA), a siRNA (small interfering RNA) or a miRNA (microRNA), but not limited thereto. By way of example, the RNA may include a RNA that is translated into protein, a RNA that is not translated into protein, a 5'-untranslated region, a 3'-untranslated region, or a regulatory RNA, but not limited thereto.

In accordance with an example embodiment, the RNA may include a miRNA, but not limited thereto. By way of example, the miRNA may involve in a biological function in a living body and may be used as a biomarker which is important in diagnosing and curing various diseases such as breast cancer, lung cancer, liver cancer, pancreatic cancer, stomach cancer, colorectal cancer, bone cancer, skin cancer, blood cancer, diabetes and Alzheimer's, or important in predicting prognosis of these diseases, but not limited thereto. By way of example, the miRNA may involve in a lineage specific differentiation in stem cell, but not limited thereto.

In accordance with an example embodiment, the miRNA may include a miRNA-21, a mi-RNA-29a, a miRNA-125b, a miRAN-155 or a miRNA-159, but not limited thereto. The miRNA-21, the miRNA-29a, the mi-RNA-125b or the miRNA-155 may be a miRNA expressed in a human cell, whereas the miRNA-159 may be a miRNA expressed in a plant cell, but not limited thereto. The miRNA-21, the miRNA-29a and the miRNA-125b may be miRNAs expressed in a breast cancer cell, but not limited thereto. For example, the miRNA-21, the miRNA-29a, the miRNA-125b or the miRNA-155 may be a miRNA expressed in a breast cancer cell line MDA-MB-231, MDA-MB-435 or MCF-7 as a model disease cell line, or from various other cancer cells, but not limited thereto.

In accordance with an example embodiment, the PNA probe may have a length of thirty (30) bases or less, but not limited thereto. By way of example, the PNA probe may have a length of about 30 bases or less, from about 5 to about 30 bases, from about 10 to about 30 bases, from about 15 to about 30 bases, from about 20 to about 30 bases, from about 25 to about 30 bases, from about 5 to about 25 bases, from about 5 to about 20 bases, from about 5 to about 15 bases, from about 5 to about 10 bases, or from about 20 to about 25 bases, but not limited thereto. For example, in case that the nucleic acid as a target material is a miRNA, the PNA probe may include about twenty two (22) bases, but not limited thereto.

In accordance with an example embodiment, the graphene oxide may be in the form of a monolayer sheet, but not limited thereto. By way of example, the graphene oxide in the form of the monolayer sheet has a larger surface area than that of graphene oxide which has the same mass but which is not in the form of a monolayer sheet. Thus, even a small quantity of graphene oxide in the form of the monolayer sheet can adsorb a large quantity of nucleic acid probe, but not limited thereto.

In accordance with an example embodiment, the graphene oxide may have a particulate form with a particle size ranging from about 10 nm to about 1 μm, but not limited thereto. By way of example, the graphene oxide may have a particle size in the range from about 10 nm to about 1 μm, from about 10 nm to about 700 nm, from about 10 nm to about 500 nm, from about 10 nm to about 400 nm, from about 10 nm to about 300 nm, from about 10 nm to about 200 nm, from about 10 nm to about 100 nm, from about 10 nm to about 50 nm, from about 50 nm to about 1 μm, from about 100 nm to about 1 μm, from about 200 nm to about 1 μm, from about 300 nm to about 1 μm, from about 400 nm to about 1 μm, from about 500 nm to about 1 μm, from about 700 nm to about 1 μm, from about 200 nm to about 300 nm, or about 400 nm or less, but not limited thereto. For example, due to its microscopic size, the graphene oxide can reach the inside of a cell along with the PNA probe adsorbed on the surface thereof while penetrating a cell membrane easily.

In accordance with an example embodiment, the nucleic acid as the target material may be present in a cell, but not limited thereto. For example, the cell may include a cell being incubated while fixed on a substrate, a cell being incubated while floating in a medium, a cell within a living body, a cell extracted from a living body, or a cell treated for analysis, but not limited thereto. For example, the cell may include a living cell or a dead cell, or may include a cell fixed by a fixing agent, but not limited thereto.

In accordance with an example embodiment, the nucleic acid as a target material may be detected in real time by measuring the fluorescence of the fluorescent material, but not limited thereto. By way of example, the fluorescence of the fluorescent material may be measured by various methods such as flow cytometry (fluorescence activated cell sorter (FACS)), fluorescence image analysis, and real-time PCR, but not limited thereto. For example, the detection may be performed for a fixed cell, a unfixed cell, a living cell, a dead cell, or a cell processed for detection, but not limited thereto.

In accordance with an example embodiment, the PNA probe may include one or more types of PNA probes containing different kinds of fluorescent materials, respectively, and the nucleic acid as the target material include one or more types of nucleic acids to be combined with the one or more types of PNA probes, respectively. Thus, multiplexed-detection of the different types of nucleic acid can be performed, but not limited thereto. By way of example, the different kinds of fluorescent materials may be fluorescent materials having different colors, but not limited thereto. By way of example, in case that the PNA probe is one or more types of probes containing different kinds of fluorescent materials and the nucleic acid as the target material is one or more types of nucleic acids having complementary sequences to those of the RNA probes, respectively, only a PNA probe having a complementary sequence to that of a nucleic acid existing in a sample would form a double strand and be separated from the graphene oxide, so that fluorescent light would emitted. Accordingly, only a fluorescent material contained in the PNA probe complementary to the nucleic acid existing in the sample would emit fluorescent light. Thus, it can be detected which one of the one or more types of nucleic acids exists in the sample by observing the color of the emitted fluorescent light.

In accordance with a second aspect of the present disclosure, there is provided a method of detecting a nucleic acid, including: a step of mixing a composition for detecting a nucleic acid with a sample including a nucleic acid as a target material, wherein the composition includes a PNA probe adsorbed on a graphene oxide and containing a fluorescent material; and a step of detecting a fluorescent light emitted from the fluorescent material, wherein the nucleic acid as a target material is combined with the PNA probe so that the PNA probe is separated from the graphene oxide and the fluorescent light is emitted from the fluorescent material.

FIG. 1 is a schematic diagram for describing a method of detecting a nucleic acid in accordance with an example embodiment.

Referring to FIG. 1, a single-stranded PNA probe contains a fluorescent material and thus can be labeled. The single-stranded PNA probe may be adsorbed on the graphene oxide through a pi-pi boding between exposed bases of the PNA probe and a hydrophobic surface of the graphene oxide.

At this time, the graphene oxide may incur FREF (Fluorescence Resonance Energy Transfer) and is capable of quenching fluorescent light of the fluorescent material contained in the PNA probe. Accordingly, the PNA probe adsorbed on the graphene oxide does not emit fluorescent light. If the graphene oxide with the PNA probe adsorbed thereon is applied to the sample, the nucleic acid as the target material present in the sample and the single-stranded PNA probe may be hybridized.

Especially, in case that the sample is a cell, due to the microscopic size of the graphene oxide and the presence of the hydrophobic portion on the surface of the graphene oxide, the graphene oxide on which the PNA probe is adsorbed can reach the inside of a cytoplasm through a cell membrane of the cell and can access a nucleic acid as the target material. As a result, the PNA probe adsorbed on the surface of the graphene oxide can be hybridized with the nucleic acid as the target material. If the PNA probe is hybridized with the nucleic acid so as to form double strands, the PNA probe would be separated from the graphene oxide. Accordingly, the fluorescent material contained in the PNA probe would be free from the FRET (Fluorescence Resonance Energy Transfer) phenomenon and may emit fluorescent light. By measuring the fluorescent light, the nucleic acid as the target material present in the sample can be detected and quantified in real time. For example, the fluorescence of the fluorescent material included in the PNA probe may be detected by, but not limited to, a flow cytometer (fluorescence activated cell sorter (FACS)), a fluorescence reader, a qRT-PCR (quantitative real-time PCR), a fluorescence microscope, an in vivo imaging device, or the like. By way of example, the fluorescence reader may be a microplate reader capable of detecting fluorescent light in the range from about 230 nm to about 999 nm, but not limited thereto. For example, the fluorescence reader may be a device configured to select about three types of organic fluorescent pigments to minimize a cross-talk phenomenon between fluorescence signals and observe the fluorescence signals, but not limited thereto. As one example, the flow cytometer may be a device capable of observing a fluorescence signal during flowing a single cell into a tube, but not limited thereto. For instance, the fluorescence microscope may include one capable of observing fluorescence inside or outside a cell or fluorescence of a sample, but not limited thereto. For example, the in vivo imaging device may be Xenogen IVIS 100 produced by Caliper Life Science Inc., but not limited thereto. For more examples, the in vivo imaging device may be a device capable of acquiring an image suitable for each fluorescence wavelength by using a CCD (Charge Coupled Device) camera, but not limited thereto.

In accordance with an example embodiment, the nucleic acid may include a DNA or RNA, but not limited thereto. By way of example, if the PNA probe containing the fluorescent material is adsorbed on the graphene oxide and introduced into a sample in which a DNA or RNA as a target material exists in the sample, the RNA probe having a complementary sequence to that of the DNA or RNA may be hybridized with the DNA or RNA and turn into a double-stranded nucleic acid. As a result, the PNA probe would be separated from the graphene oxide and the fluorescent material contained in the PNA probe emits fluorescent light without being subjected to FRET (Fluorescence Resonance Energy Transfer). Thus, by measuring the fluorescent light, the DNA or RNA existing in the sample can be detected but not limited thereto. For example, the DNA may include a DNA that encodes protein or a DNA that does not encode protein, but not limited thereto. By way of example, the RNA may include mRNA (messenger RNA), a tRNA (transfer RNA), a rRNA (ribosomal RNA), a s RNA (small RNA), a snRNA (small nuclear RNA), a scRNA (small cytoplasmic RNA), a siRNA (small interfering RNA) or a miRNA (microRNA), but not limited thereto. By way of example, the RNA may include a RNA that is translated into protein, a RNA that is not translated into protein, a 5'-untranslated region, a 3'-untranslated region, or a regulatory RNA, but not limited thereto.

In accordance with an example embodiment, the RNA may include a miRNA, but not limited thereto. By way of example, the miRNA may involve in a biological function in a living body and may be used as a biomarker which is important in diagnosing and curing various diseases such as breast cancer, lung cancer, liver cancer, pancreatic cancer, stomach cancer, colorectal cancer, bone cancer, skin cancer, blood cancer, diabetes and Alzheimer's, or important in predicting prognosis of these diseases, but not limited thereto. By way of example, the miRNA may involve in a lineage specific differentiation in stem cell, but not limited thereto.

In accordance with an example embodiment, the miRNA may include a miRNA-21, a mi-RNA-29a, a miRNA-125b, a miRAN-155 or a miRNA-159, but not limited thereto. The miRNA-21, the miRNA-29a, the mi-RNA-125b or the miRNA-155 may be a miRNA expressed in a human cell, whereas the miRNA-159 may be a miRNA expressed in a plant cell, but not limited thereto. The miRNA-21, the miRNA-29a and the miRNA-125b may be miRNAs expressed in a breast cancer cell, but not limited thereto. For example, the miRNA-21, the miRNA-29a, the miRNA-125b or the miRNA-155 may be a miRNA expressed in a breast cancer cell line MDA-MB-231, MDA-MB-435 or MCF-7 as a model disease cell line, or from various other cancer cells, but not limited thereto.

In accordance with an example embodiment, the PNA probe may have a length of thirty (30) bases or less, but not limited thereto. By way of example, the PNA probe may have a length of about 30 bases or less, from about 5 to about 30 bases, from about 10 to about 30 bases, from about 15 to about 30 bases, from about 20 to about 30 bases, from about 25 to about 30 bases, from about 5 to about 25 bases, from about 5 to about 20 bases, from about 5 to about 15 bases, from about 5 to about 10 bases, or from about 20 to about 25 bases, but not limited thereto. For example, in case that the nucleic acid as a target material is a miRNA, the PNA probe may include about twenty two (22) bases, but not limited thereto.

In accordance with an example embodiment, the graphene oxide may be in the form of a monolayer sheet, but not limited thereto. By way of example, the graphene oxide in the form of the monolayer sheet has a larger surface area than that of graphene oxide which has the same mass but which is not in the form of a monolayer sheet. Thus, even a small quantity of graphene oxide in the form of the monolayer sheet can adsorb a large quantity of nucleic acid probe, but not limited thereto.

In accordance with an example embodiment, the graphene oxide may have a particulate form with a particle size ranging from about 10 nm to about 1 μm, but not limited thereto. By way of example, the graphene oxide may have a particle size in the range from about 10 nm to about 1 μm, from about 10 nm to about 700 nm, from about 10 nm to about 500 nm, from about 10 nm to about 400 nm, from about 10 nm to about 300 nm, from about 10 nm to about 200 nm, from about 10 nm to about 100 nm, from about 10 nm to about 50 nm, from about 50 nm to about 1 μm, from about 100 nm to about 1 μm, from about 200 nm to about 1 μm, from about 300 nm to about 1 μm, from about 400 nm to about 1 μm, from about 500 nm to about 1 μm, from about 700 nm to about 1 μm, from about 200 nm to about 300 nm, or about 400 nm or less, but not limited thereto. For example, due to its microscopic size, the graphene oxide can reach the inside of a cell along with the PNA probe adsorbed on the surface thereof while penetrating a cell membrane easily.

In accordance with an example embodiment, the sample may include a cell, but not limited thereto. For example, the cell may include a cell being incubated while fixed on a substrate, a cell being incubated while floating in a medium, a cell within a living body, a cell extracted from a living body, or a cell treated for analysis, but not limited thereto. For example, the cell may include a living cell or a dead cell, or may include a cell fixed by a fixing agent, but not limited thereto.

In accordance with an example embodiment, the nucleic acid as a target material in the sample may be detected in real time by measuring the fluorescence of the fluorescent material in real time. By way of example, the fluorescence of the fluorescent material may be measured by various methods such as flow cytometry [fluorescence activated cell sorter (FACS)], fluorescence image analysis, and real-time PCR, but not limited thereto. For example, the detection may be performed for a fixed cell, a unfixed cell, a living cell, a dead cell, or a cell processed for detection, but not limited thereto.

In accordance with an example embodiment, the PNA probe may include one or more types of PNA probes containing different kinds of fluorescent materials, respectively, and the nucleic acid as the target material include one or more types of nucleic acids to be combined with the one or more types of PNA probes, respectively. Thus, multiplexed-detection of the different types of nucleic acid can be performed, but not limited thereto. By way of example, the different kinds of fluorescent materials may be fluorescent materials having different colors, but not limited thereto. By way of example, in case that the PNA probe is one or more types of probes containing different kinds of fluorescent materials and the nucleic acid as the target material is one or more types of nucleic acids having complementary sequences to those of the RNA probes, respectively, only a PNA probe having a complementary sequence to that of a nucleic acid existing in a sample would form a double strand and be separated from the graphene oxide, so that fluorescent light would emitted. Accordingly, only a fluorescent material contained in the PNA probe complementary to the nucleic acid existing in the sample would emit fluorescent light. Thus, it can be detected which one of the one or more types of nucleic acids exists in the sample by observing the color of the emitted fluorescent light.

Below, examples of the embodiments will be described. However, the following examples are intended to facilitate understanding of the present disclosure and therefore are not intended to limit its scope.

EXAMPLES

Example 1

Preparation and Characterization of Graphene Oxide

In an example, a graphene oxide sheet was prepared according to the modified Hummer's method which is commonly known in the pertinent art. First, 0.5 g of $NaNO_3$ (produced by Junsei Co., (Japan)) and 23 mL of $H_2SO_4$ (produced by Samchun Chemical Co., (Seoul, Korea) were mixed while being intensely agitated within a water tub filled with ice. Then, 3 g of $KMnO_4$ (produced by Sigma-Aldrich Co., (Missouri, USA) was slowly added to the mixture. After the $KMnO_4$ is added, the solution was moved into an ice bath at a temperature of 35° C. and agitated therein for 1 hour. Then, 40 mL of distilled water was added, and the temperature of the water tub was raised to 90° C. for 30 minutes. Then, 100 mL of distilled water was added again. Thereafter, by adding 3 mL of 30% $H_2O_2$ (produced by Junsei Co., (Japan)) in drops, the color of the solution was changed from dark brown to yellow. Then, the synthesized graphene oxide solution was filtered through a Buchner funnel and washed with distilled water at least four times. Filtered sediments were dried in desiccators and re-dispersed into the distilled water. Thereafter, the solution in which the graphene oxide was dispersed was ultrasonicated for four hours, so that nano-size graphene oxide was obtained. The size of the graphene oxide obtained at this time was in the range from about 0.05 nm to about 300 nm, and this graphene oxide was stored and used in a concentration of 1 mg/mL.

Figure 2A:
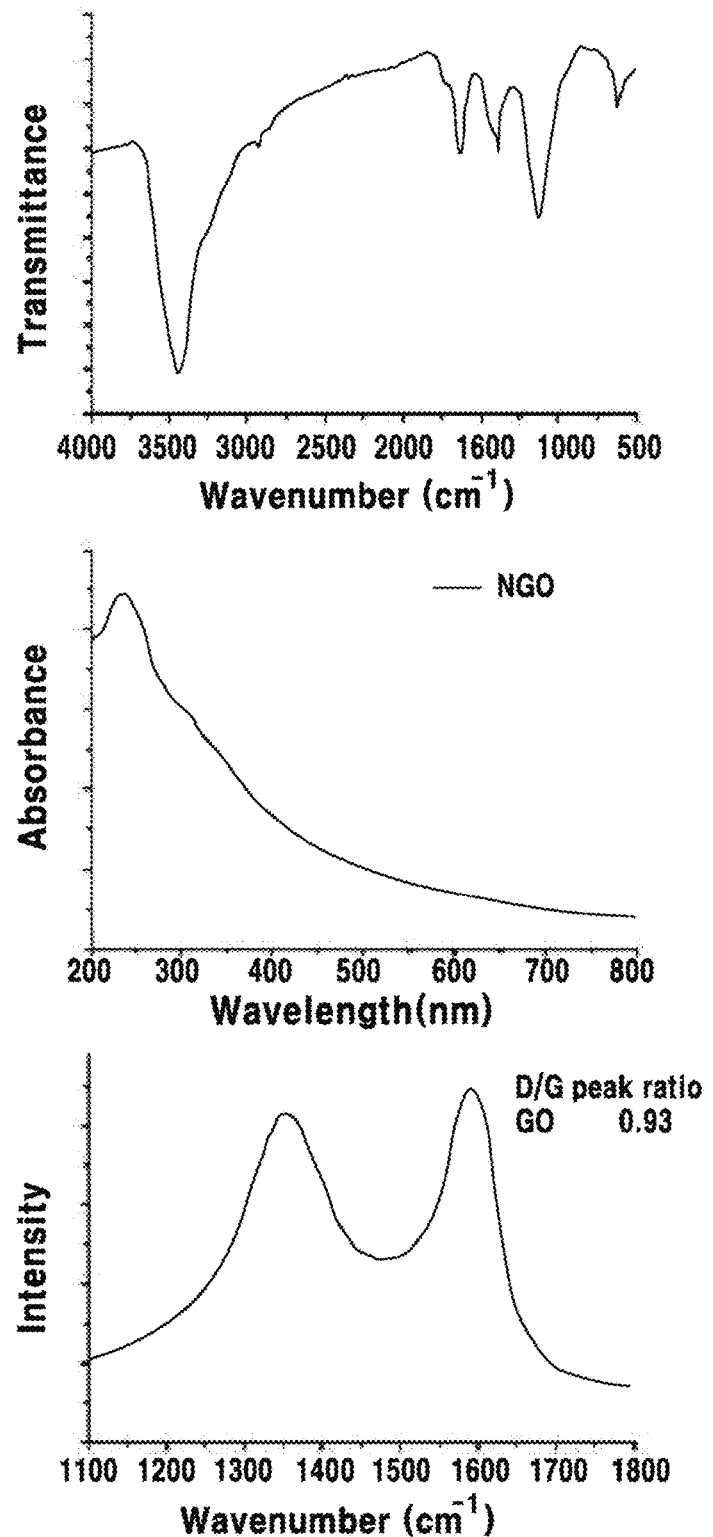
FIG. 2A provides an analysis result of ultraviolet-visible (UV-vis) spectrum of graphene oxide in an example of the present disclosure.
Figure 2B:
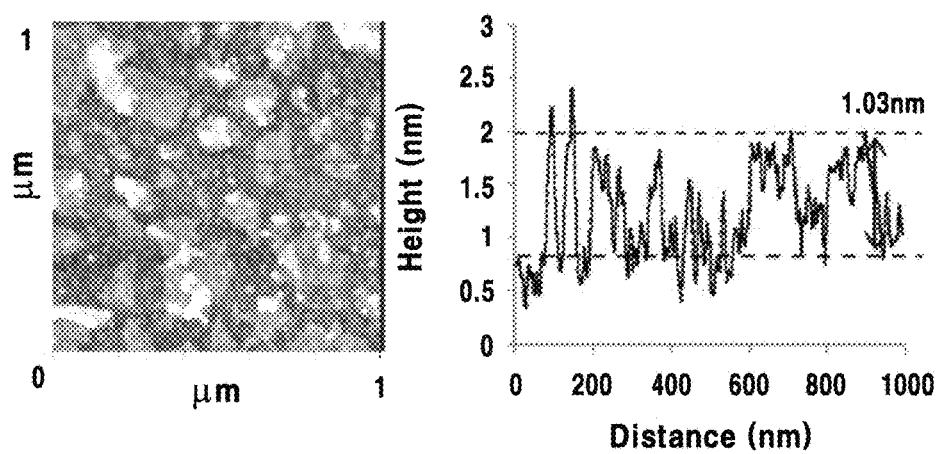
FIG. 2B provides an analysis result of a chemical structure of the graphene oxide in an example of the present disclosure.

The graphene oxide prepared according to the above method was analyzed by using atomic force microscopy (AFM) and it was confirmed that this graphene oxide is in the form of a monolayer sheet. As for a size and a thickness of the sheet, the sheet has a width of from 0.05 nm to 300 nm and a height of 1.03 nm. Further, ultraviolet-visible (UV-vis) spectrum of the graphene oxide was investigated, and an absorbance peak was observed, as well-known in the art, at 230 nm, as depicted in FIG. 2A. A chemical structure of the graphene oxide was investigated by using infrared ray and Raman spectrum, and the result is shown in FIG. 2B. Functional groups combined with the graphene oxide were found to be alcohol (3,415 cm$^{-1}$, 1,040 cm$^{-1}$), epoxy (1,079 cm$^{-1}$), carboxyl (1,716 cm$^{-1}$), oxidized sp2 carbon (1,627 cm$^{-1}$), and so forth. In view of a decrease of a relative intensity of the carboxyl group in the nano-graphene oxide preparation process, it was deemed that a reduction reaction had occurred slightly. Further, as a result of zeta-potential measurement in which surface charges were measured, a negative value of −17.9 mV was observed. As proved from these data, the graphene oxide mono-layer sheet was prepared successfully.

Example 2

Adsorption of a Single-Stranded PNA Probe to Graphene Oxide and Observation of Resultant Fluorescence Quenching Sequences of miRNAs and complementary sequences of PNA probes used in the present example and all of the following examples are specified in Table 1 as bellows.

TABLE 1

| Target miRNA | Base Sequence of miRNA | Base Sequence of Fluorescence-labeled Probe | Organism |
|---|---|---|---|
| miRNA-21 | UAGCUUAUCAGACUGAUG UUGA (SEQ ID No. 1) | FAM-OO-TCAACATCAGTCTGAT AAGCTA (SEQ ID No. 6) | Human |
| miRNA-125b | UCCCUGAGACCCUAACUU GUGA (SEQ ID No. 2) | ROX-OO-TCACAAGTTAGGGTCT CAGGGA (SEQ ID No. 7) | Human |
| miRNA-155 | UUAAUGCUAAUCGUGAUA GGGGU (SEQ ID No. 3) | Cy5-OO-CTATCACGATTAGCAT TA (SEQ ID No. 8) | Human |
| miRNA-159 | UUUGGAUUGAAGGGAGCU CUA (SEQ ID No. 4) | FAM-OO-TAGAGCTCCCTTCAAT CCAAA (SEQ ID No. 9) | Plant |
| miRNA-29a | UAGCACCAUCUGAAAUCG GUUA (SEQ ID No. 5) | FAM-OO-TAACCGATTTCAGATG GTGCTA (SEQ ID No. 10) | Human |

In the above table, the left sequences of nucleic acids are base sequences of miRNAs, whereas the right sequences of nucleic acids are base sequences of PNA probes that are complementary to the respective base sequences of the miRNAs. The miRNA-159 was used as a negative control group. The miRNA used in this example include a miRNA-21, a miRNA-29a, a miRNA-125b and a miRNA-155 that are known to be expressed in several cancer cells including breast cancer.

In this example, three kinds of single-stranded PNA probes labeled with organic fluorescent pigments FAM, ROX and Cy5, respectively, were dissolved in nuclease-free water of which the concentration of single-stranded PNA is 100 μM. Selected as the three kinds of PNA probes, a miRNA-21, a miRNA-125b and a miRNA-155 were showing different expression patterns on breast cancer cell lines (MDA-MB-231, MDA-MB-435, and MCF-7) as model disease cell lines. At this time, in consideration of an in vivo experiment as well as an in vitro experiment, the PNA probes were dissolved in the nuclease-free water. Further, since the solubility of the PNA probes would be different depending on their base sequences, lengths, and the like, the PNA probes were dissolved after being heated at a temperature of from about 60° C. to 70° C. for about 10 minutes. Then, the PNA solutions were divided into each amount of usage and stored in a cold storage while wrapped in foil. Whenever each PNA solution is used, it was heated at the temperature of from about 60° C. to 70° C. for about 10 minutes, as mentioned above. Then, the fluorescence-labeled PNA probes were mixed with the nano-size graphene oxide, respectively (such that the graphene oxide which was prepared to have a concentration of from 0.5 mg/mL to 1 mg/mL reached a concentration of from 0.05 mg/mL to 0.1 mg/mL). When mixing each fluorescence-labeled PNA probe and the graphene oxide, a buffer (250 mM Tris, pH 7.4 (Fisher Co.,)) enriched to five times was added to the PNA probe and the graphene oxide in proportion to the total volume of each solution, and the rest volume was filled with the nuclease-free water.

As a result of mixing the fluorescence-labeled PNA probes and the graphene oxide, it was observed that from about 190 pmol to about 200 pmol of FAM-PNA-21 (PNA probe containing a FAM fluorescent material and complementary to the miRNA-21) could be adsorbed to each 1 μg of nano-size graphene oxide (nGO); about 135 pmol of ROX-PNA-125b (PNA probe containing a ROX fluorescent material and complementary to the miRNA-125b) could be adsorbed to each 1 μg of nano-size graphene oxide (nGO); and about 180 pmol of Cy5-PNA-155 (PNA probe containing a Cy5 fluorescent material and complementary to the miRNA-155) could be adsorbed to each 1 μg of nano-size graphene oxide (nGO).

Figure 3:
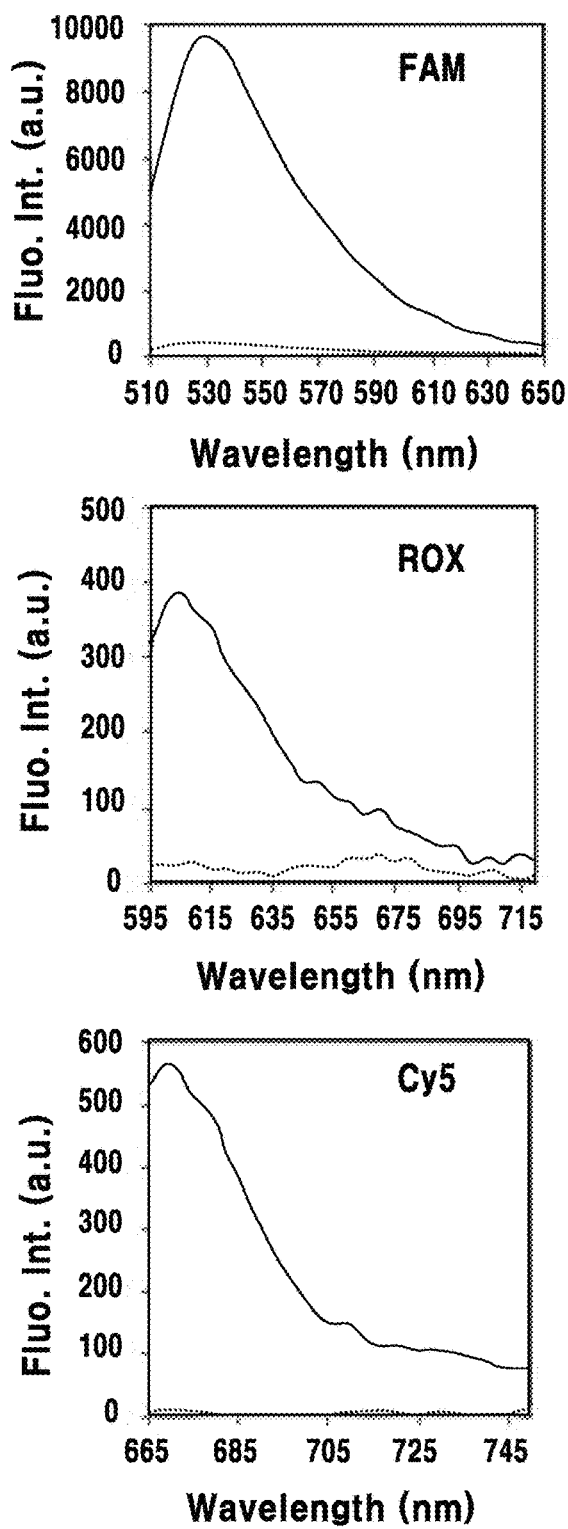
FIG. 3 is a graph showing adsorption of a PNA probe to graphene oxide and occurrence or non-occurrence of fluorescence quenching in an example of the present disclosure.

Then, fluorescence in each case was analyzed by using a fluorescence reader (Biotek Synergy MX). As depicted in FIG. 3, a fluorescence signal of FAM, a fluorescence signal of ROX and a fluorescence signal of Cy5 exhibited the highest fluorescence peak at ex/em=488/530 nm, ex/em=575/610 nm and ex/em=643/670 nm, respectively. In the present example, the fluorescence was observed with the spectrum in this range. Here, if the fluorescence signal of each probe when the probe is not mixed with the graphene oxide is set as 100%, it is deemed to be optimal when the fluorescence signal quenched and decreased to about 4% of the original signal. When the graphene oxide and the FAM-PNA-21, the ROX-PNA-125b or the Cy5-PNA-155 were mixed, it was confirmed through fluorescence observation that the fluorescence signal of the PNA probe quenched effectively at a room temperature in about 10 minutes.

Example 3

Evaluation of Oligonucleic Acid Containing a Fluorescent Material, for Detecting miRNA as a Target Material Numerous biomolecules exist in a cell. Therefore, in case of graphene oxide having high adsorbability for nonspecific biomolecules, non-specific desorption of a probe may be occur even under the absence of a nucleic acid as a target material, thus emitting a fluorescence signal. In view of this, in the present example, miRNA detection efficiencies of a PNA probe or DNA probe having a base sequence complementary to that of a target miRNA were compared to investigate whether the PNA probe is more suitable than the DNA probe.

Cells of MDA-MB-231 expressing the miRNA-21 as one of breast cancer cell lines selected as a model disease cell line were collected, and a cytolysate was acquired by repeating freezing an defrosting of the cells. A DNA or PNA probe complementary to the miRNA-21 was used while labeling the DNA or PNA probe with an organic fluorescent pigment FAM.

Figure 4:
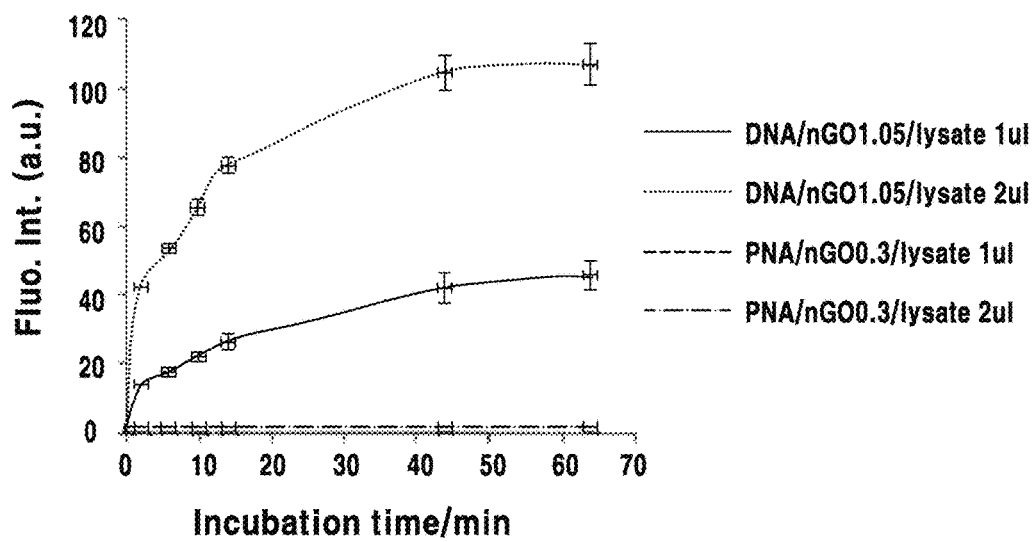
FIG. 4 is a graph for the comparison of a quenching phenomenon of a PNA probe and a quenching phenomenon of a DNA probe in an example of the present disclosure.
Figure 4:
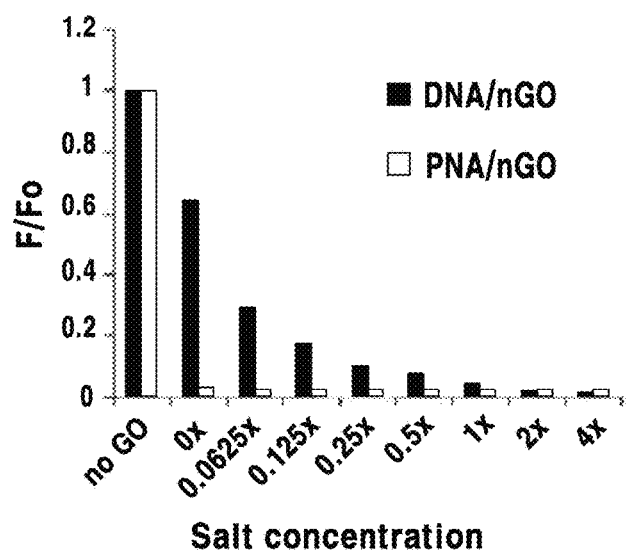

A buffered hypotonic solution (20 mM of HEPES (pH 8.0), 2 mM of $MgCl_2$, 0.2 mM of EGTA, 10% of glycerol and 1 mM of dethiothreitol, and 1 mM of DTT was added immediately before used) for cell lysis was prepared, and a hundred thousand (100,000) cells were in 100 L of the buffer solution. Then, by repeating freezing and defrosting of the cell-containing solution about three times by subjecting the cell-containing solution to liquid nitrogen (temperature of about −196° C.) and a temperature of 37° C. alternately, the cells were broken down and cell lysate was obtained. Then, 15 μL of 3M NaCl was added to 100 μL of the obtained lysate, and a final NaCl concentration was set to 4 M. Thereafter, the mixture was centrifugated at a 12,000 rpm by a centrifuge of 4° C. for about 20 minutes. A supernatant was moved into a new storage tube and used in an experiment. Each of a DNA probe and a PNA probe (FAM-PNA-21) complementary to the miRNA-21 was adsorbed on graphene oxide, and the DNA and PNA probes adsorbed on the graphene oxide were subjected to experiment while mixed with the cell lysate. In the present example, the degree of fluorescence quenching of the fluorescent light labeled in the probe, which depends on a variation in the concentration of a salt was tested. As shown in FIG. 4, the DNA probe showed a variation in the degree of fluorescence quenching depending on a variation in the concentration of the salt. Unlike the DNA probe, however, the PNA probe showed a constant degree of quenching regardless of the salt concentration. Further, in the process of cell lysis by repeating the freezing and defrosting of the cells, it was confirmed that after mixed with the cell lysate in which most RNAs were decomposed and no more existed, the DNA probe was easily separated from the graphene oxide and fluorescence dequenched, whereas the PNA probe was stably adsorbed on the graphene oxide and maintain the fluorescence quenching state. That is, it is deemed that the DNA probe adsorbed on the graphene oxide would be easily separated from the graphene oxide even under the absence of a miRNA as a target, unlike the PNA probe. Thus, it was proved that the PNA probe can be adsorbed on the graphene oxide more stable than the DNA probe.

Example 4

Figure 5A:
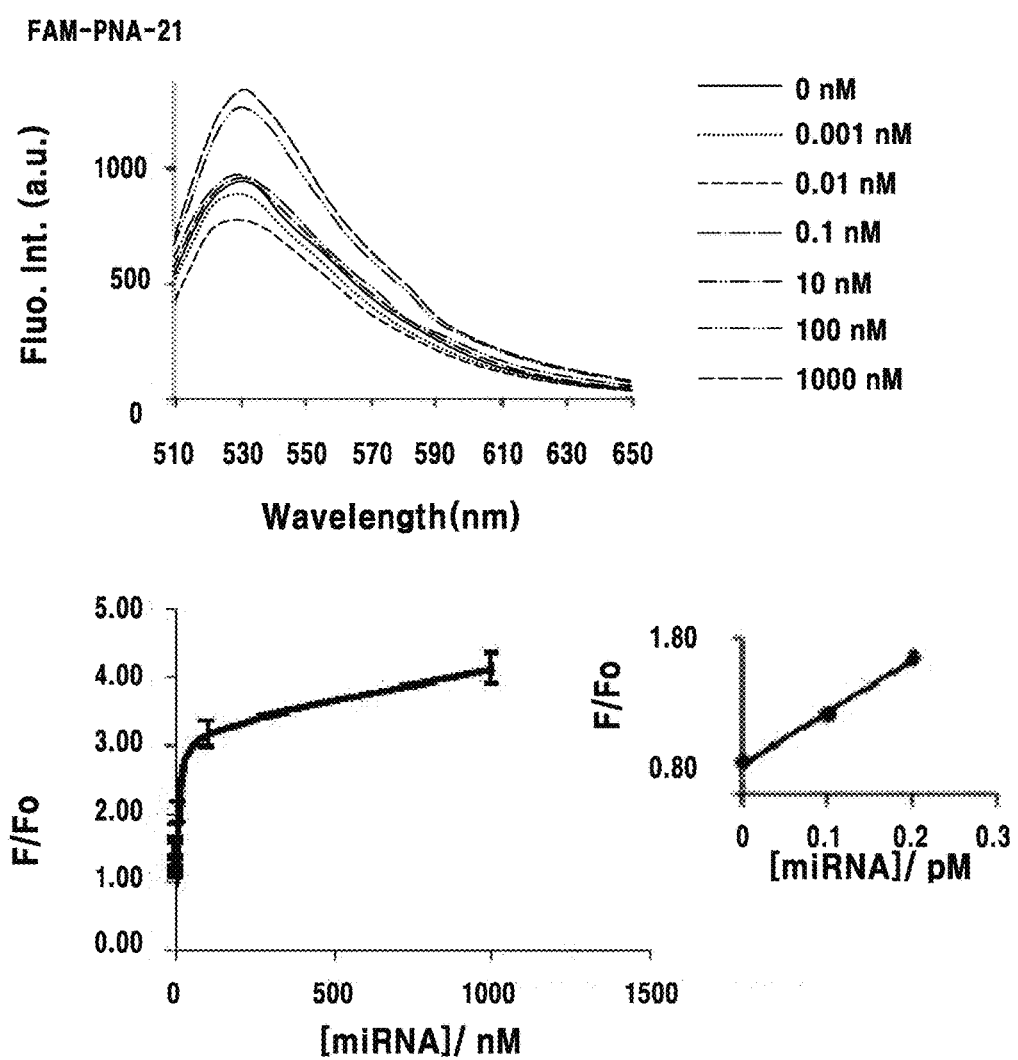
FIG. 5A is a graph showing a measurement of sensitivity of a PNA probe to a miRNA in an example of the present disclosure.
Figure 5B:
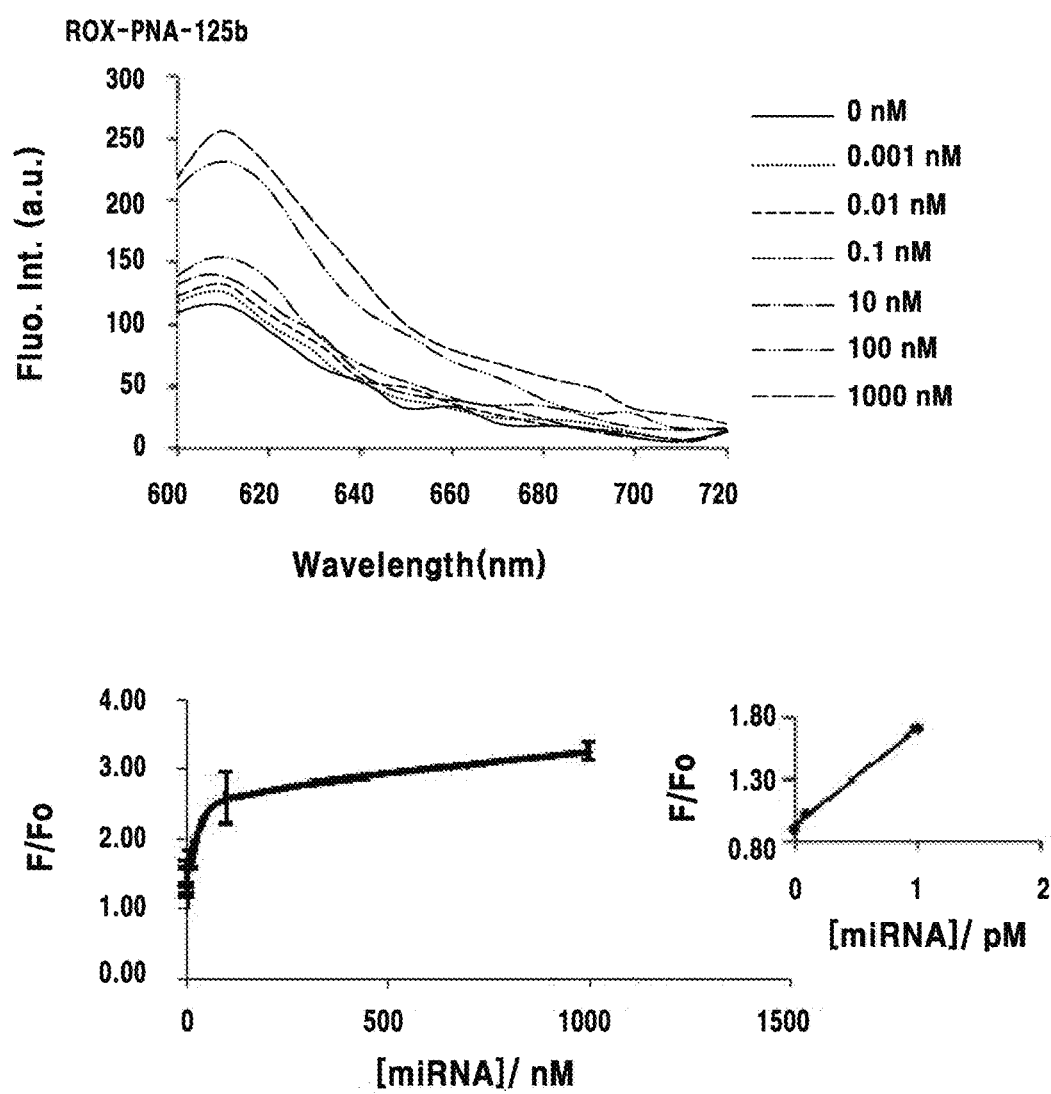
FIG. 5B is a graph showing a measurement of sensitivity of a PNA probe to a miRNA in an example of the present disclosure.
Figure 5C:
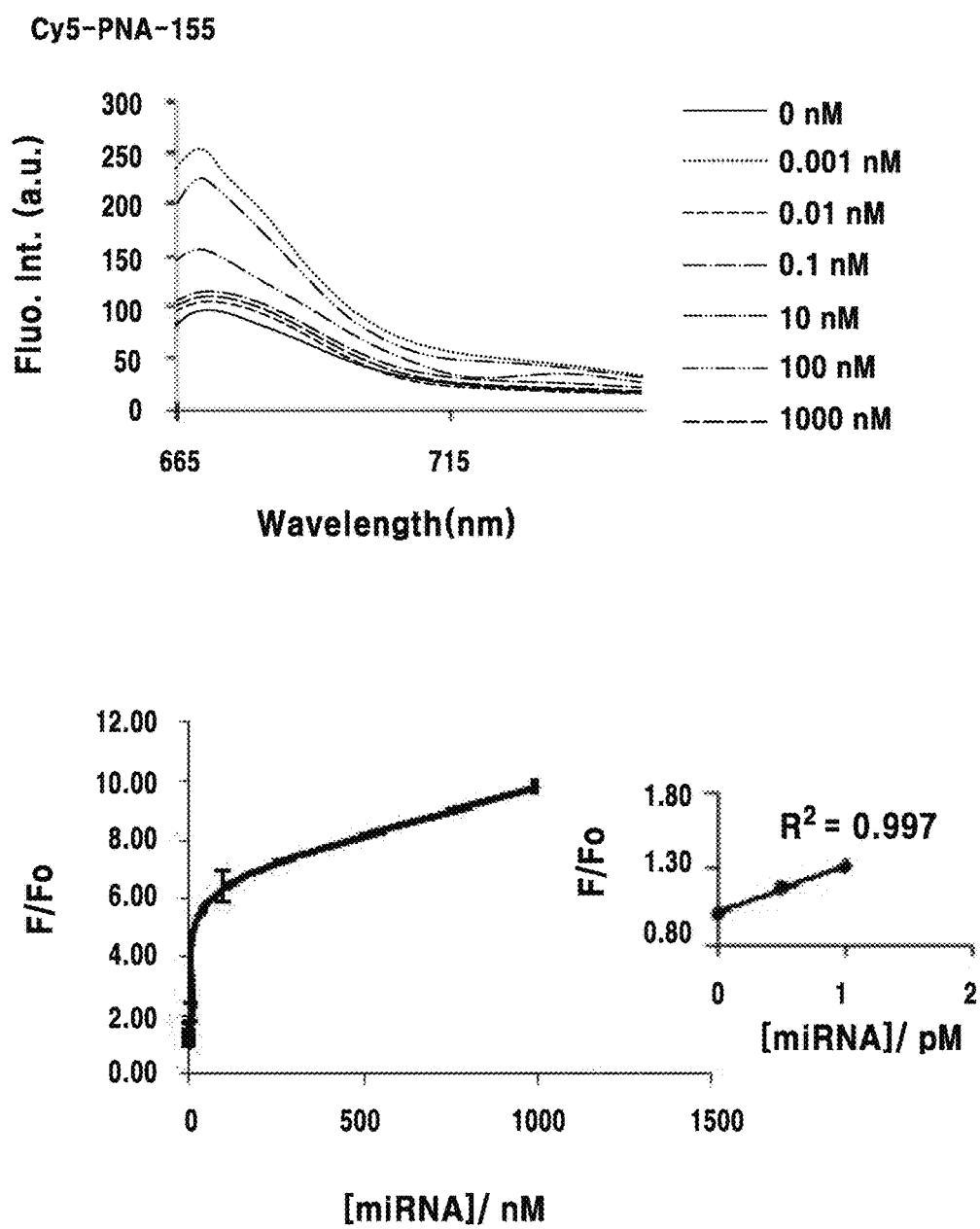
FIG. 5C is a graph showing a measurement of sensitivity of a PNA probe to a miRNA in an example of the present disclosure.

Evaluation of Detection Sensitivity of PNA Probes for a miRNA as a Target Material A total quantity of RNAs present in a single cell may be about 15 μg, and miRNAs exist therein in a much smaller quantity. Thus, detection sensitivity for a miRNA as a target material was evaluated in this example. The detection sensitivity of a PNA probe for a miRNA-21, a miRNA-125b or a miRNA-155 was evaluated as follows. A solution prepare by adsorbing a fluorescence-labeled PNA probe to 1 μg of nano-size graphene oxide was synthesized with a miRNA (produced by Bioneer Co.,) as a target material. Specifically, the miRNA was added in an amount of 0 mN, 0.001 nM, 0.01 nm, 0.1 nM, 1 nM, 10 nM, 100 nM or 1,000 nM and left at a room temperature for about 10 minutes. Then, fluorescence of a fluorescent material expressed at each probe was measured. As a result of measuring a variation in the fluorescence before and after adding the miRNA as the target material, a miRNA having a concentration in the range from about 0.1 pM to about 1 pM was detected in experiments using the three kinds of PNA probes, as depicted in FIG. 5A to FIG. 5C, though the amounts of the PNA probes adsorbed on the nano-size graphene oxide having a unitary quantity of 1 μg were different.

Example 5

Detection of a Single-Target miRNA or Multi-Target miRNAs Present in a Sample

Figure 6A:
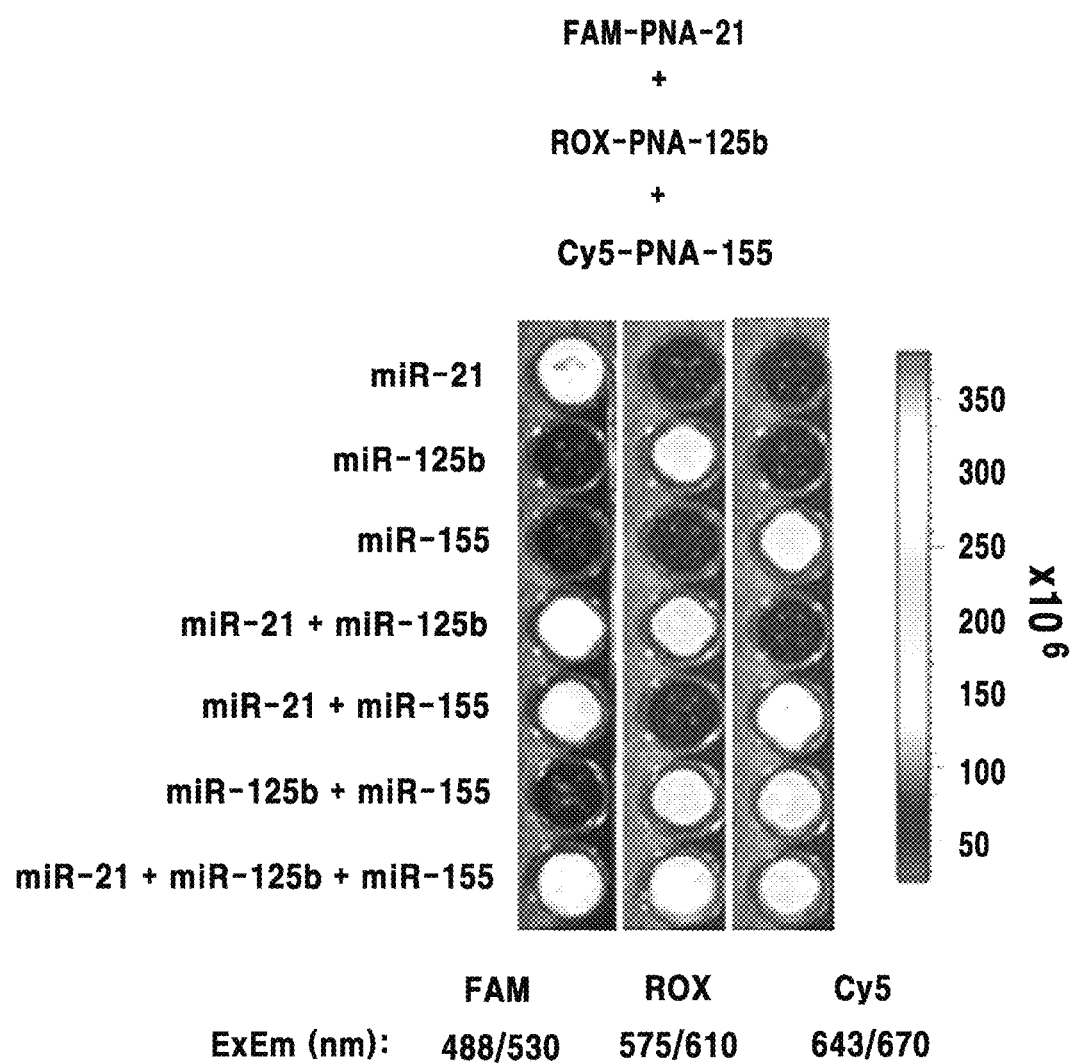
FIG. 6A shows a single-target or multi-target miRNA detection analysis result using a composition for detecting a nucleic acid in an example of the present disclosure.
Figure 6B:
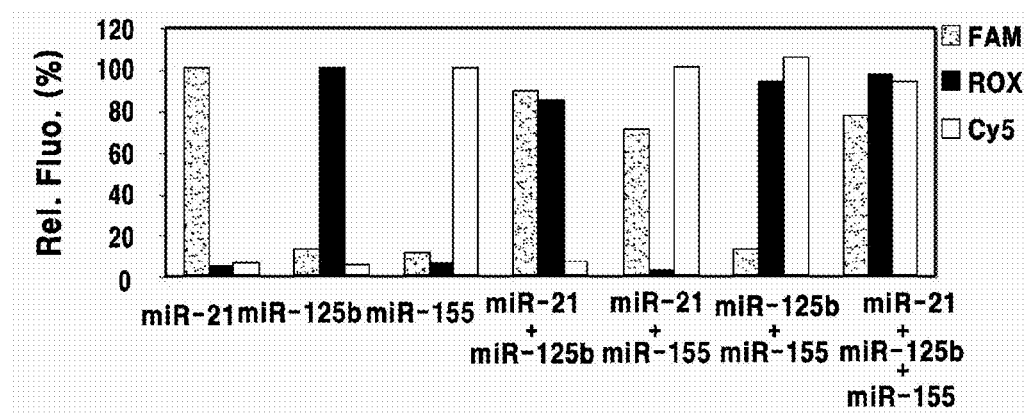
FIG. 6B shows a single-target or multi-target miRNA detection analysis result using a composition for detecting a nucleic acid in an example of the present disclosure.
Figure 6C:
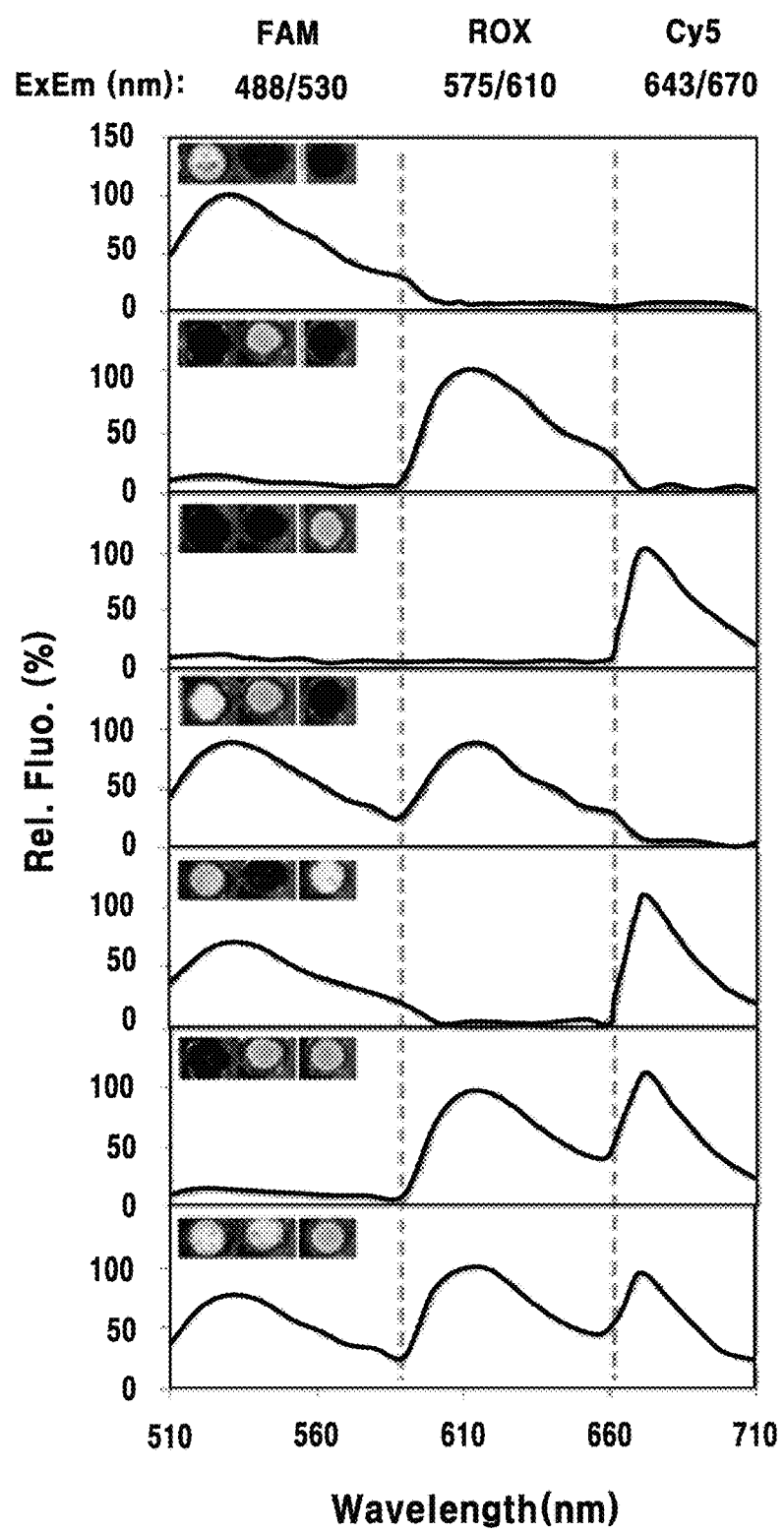
FIG. 6C shows a single-target or multi-target miRNA detection analysis result using a composition for detecting nucleic acid in an example of the present disclosure.
Figure 7A:
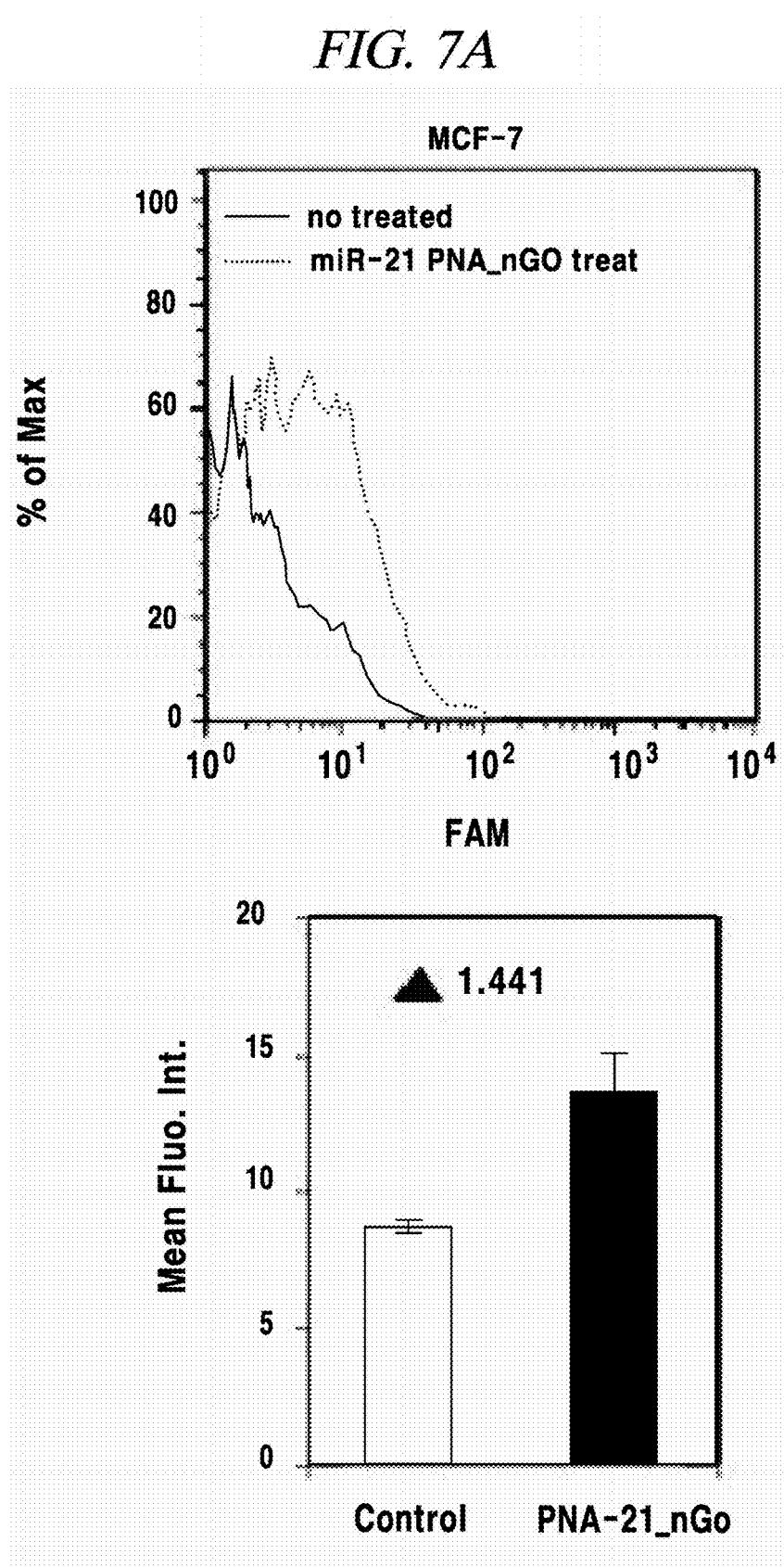
FIG. 7A shows an intracellular single-target miRNA detection analysis result using a composition for detecting a nucleic acid in an example of the present disclosure.
Figure 7B:
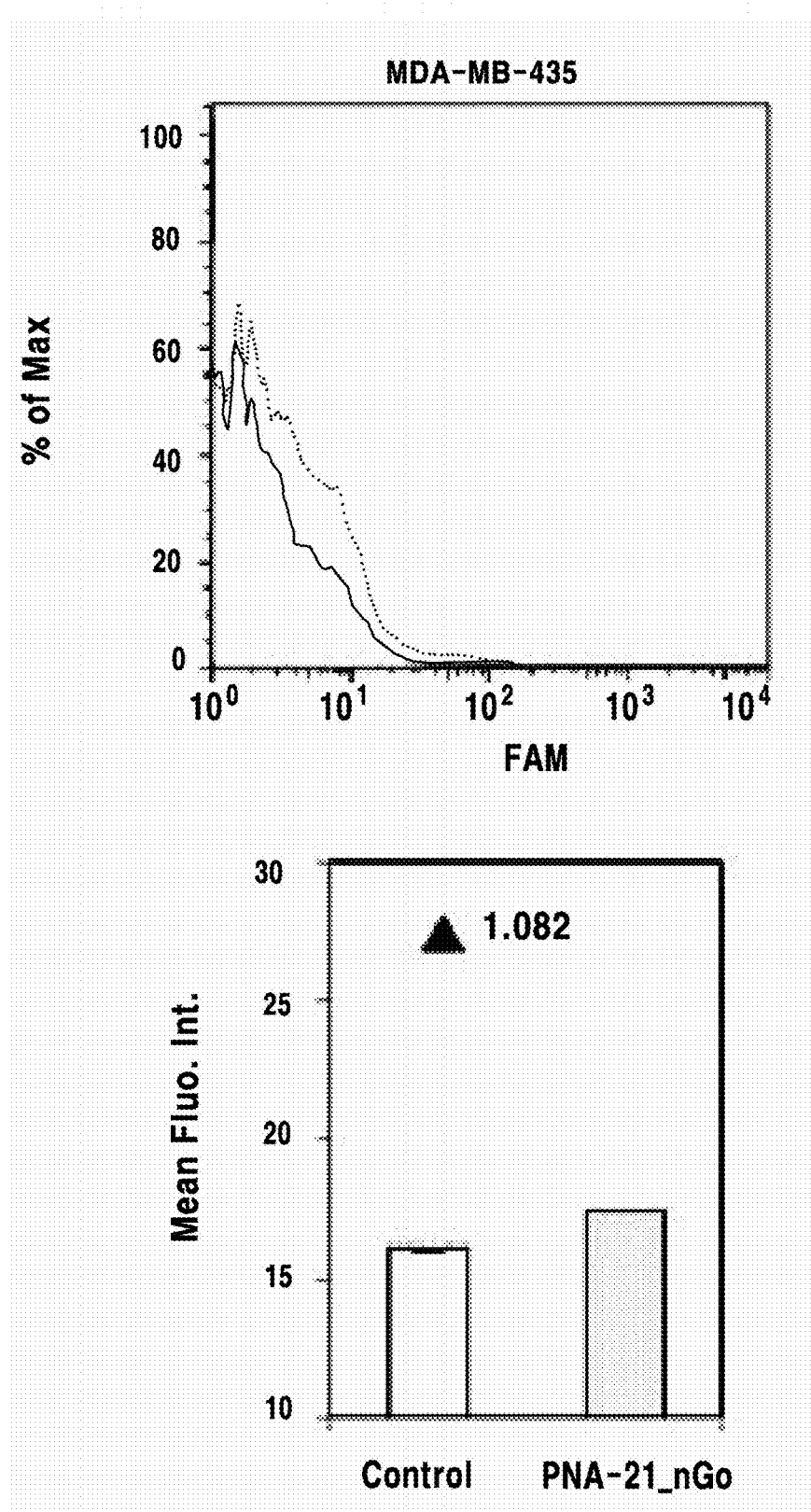
FIG. 7B shows an intracellular single-target miRNA detection analysis result using a composition for detecting a nucleic acid in an example of the present disclosure.
Figure 7C:
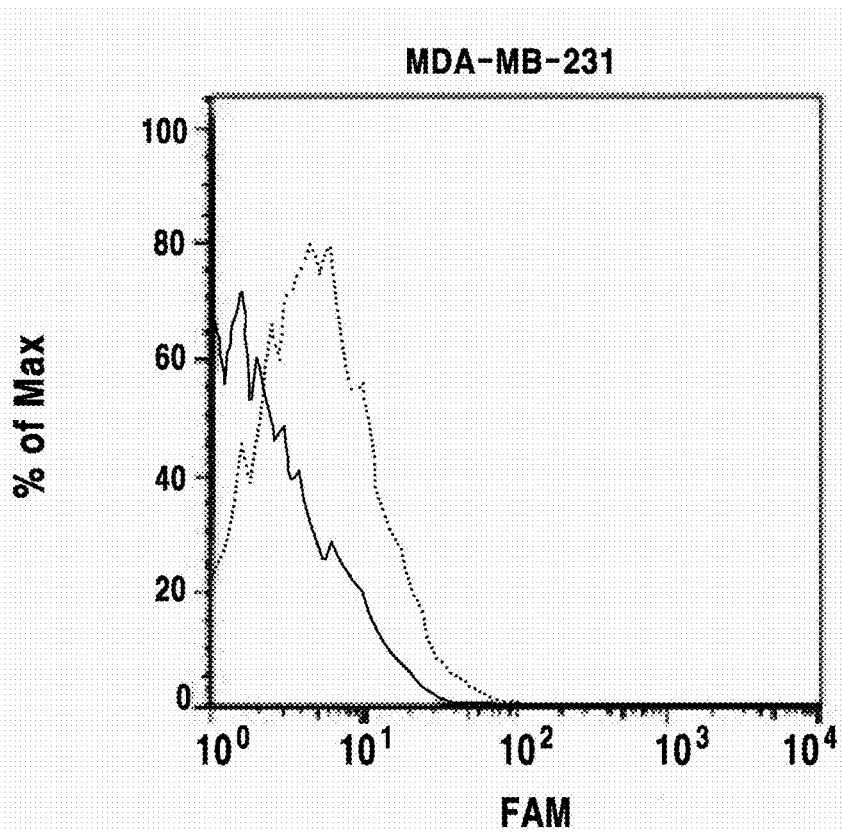
FIG. 7C shows an intracellular single-target miRNA detection analysis result using a composition for detecting a nucleic acid in an example of the present disclosure.
Figure 7C:
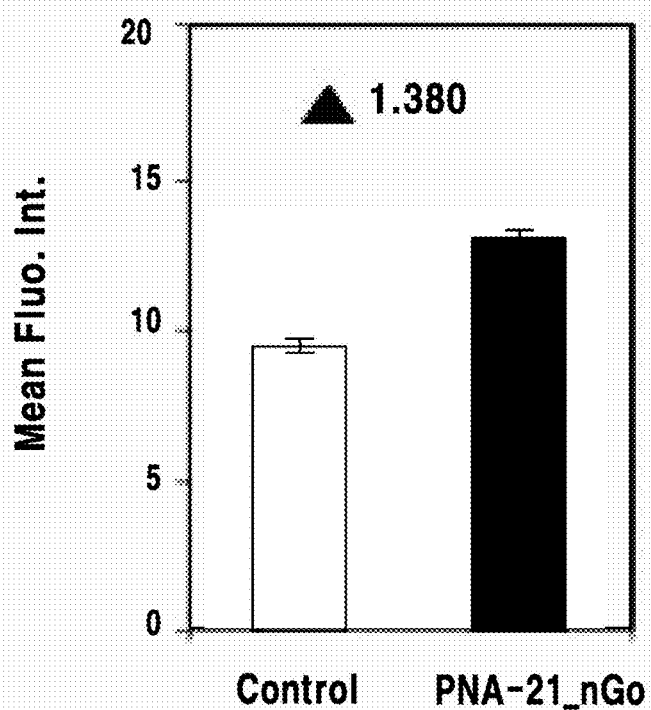
Figure 7D:
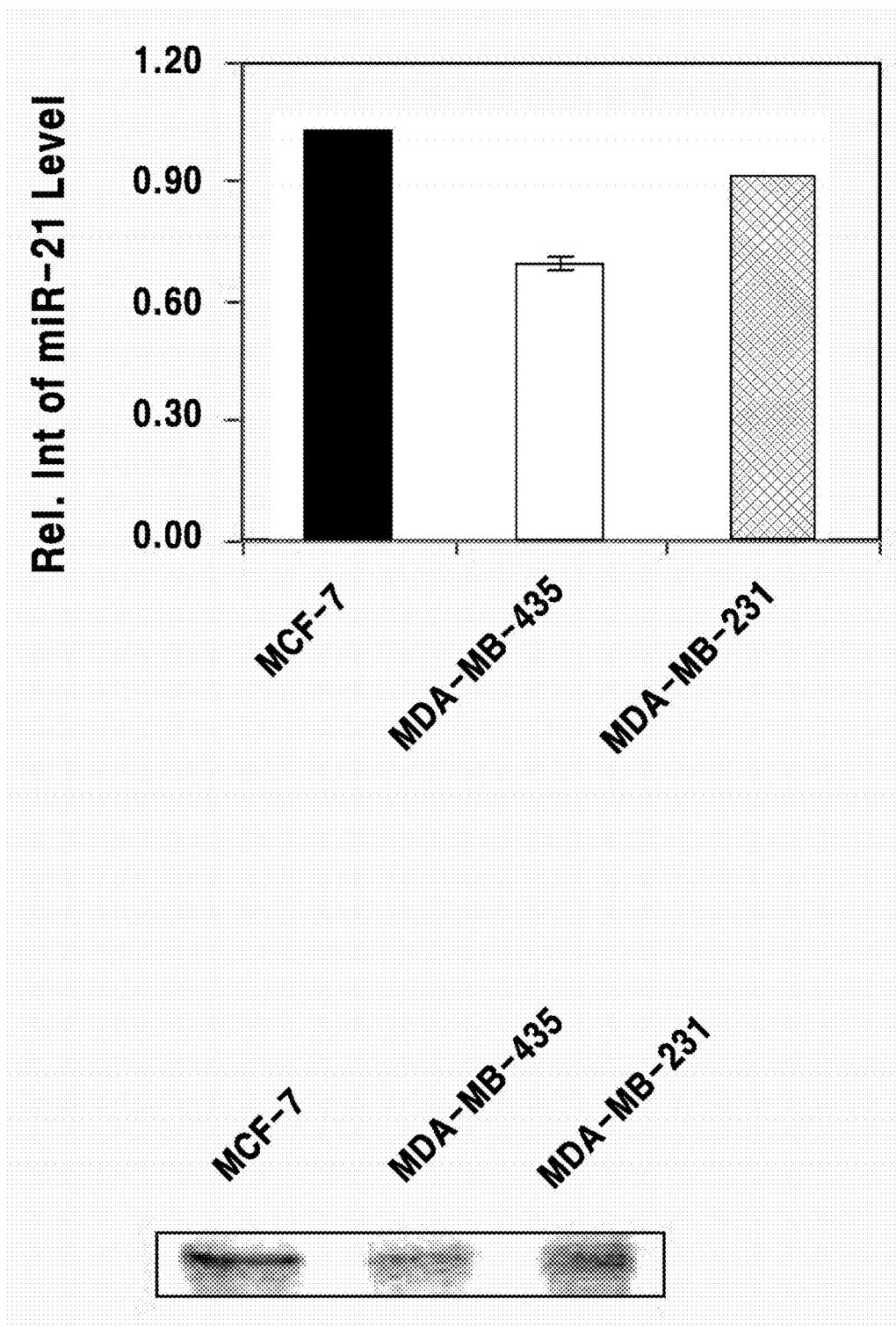
FIG. 7D shows an intracellular single-target miRNA detection analysis result using a composition for detecting a nucleic acid in an example of the present disclosure.
Figure 7E:
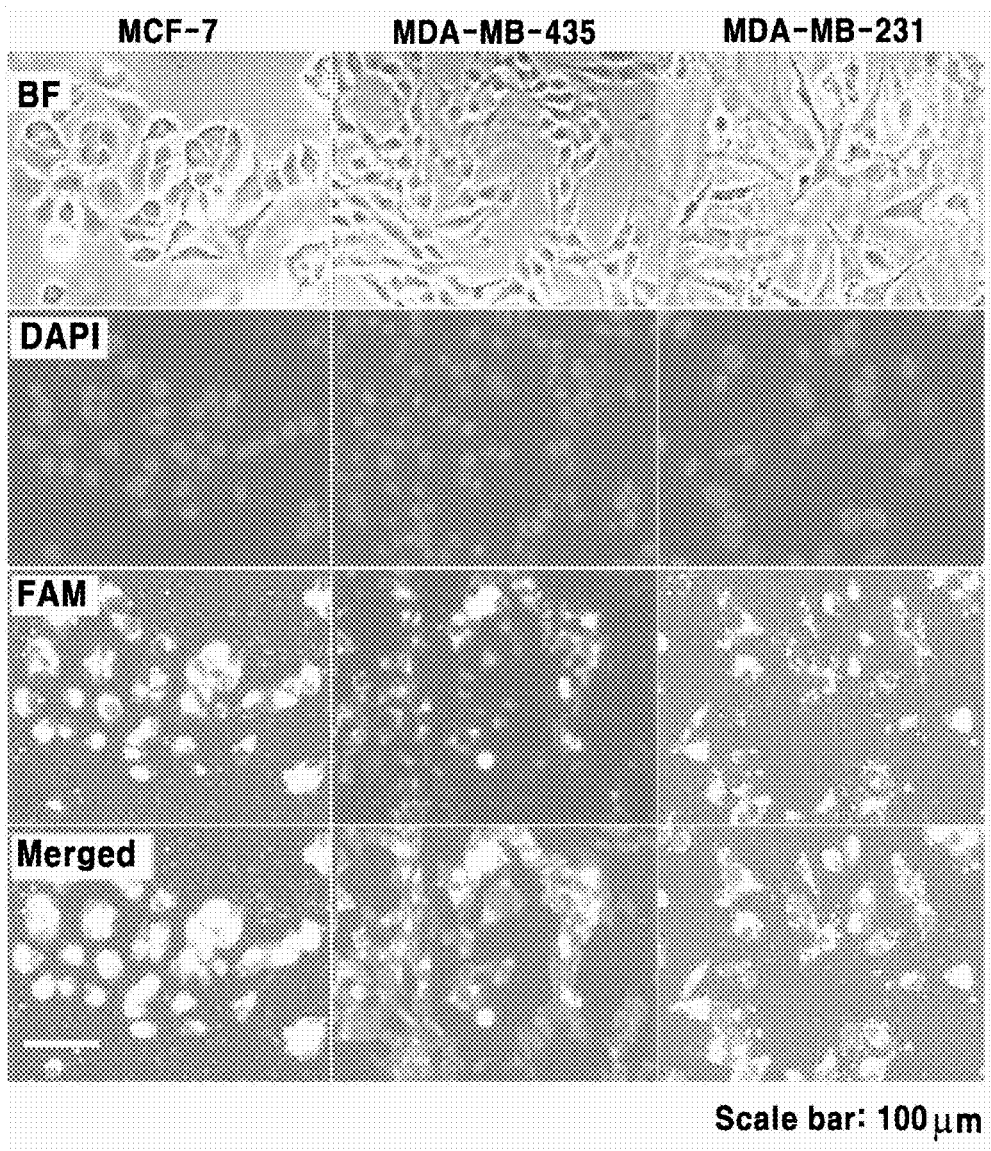
FIG. 7E shows an intracellular single-target miRNA detection analysis result using a composition for detecting a nucleic acid in an example of the present disclosure.
Figure 8A:
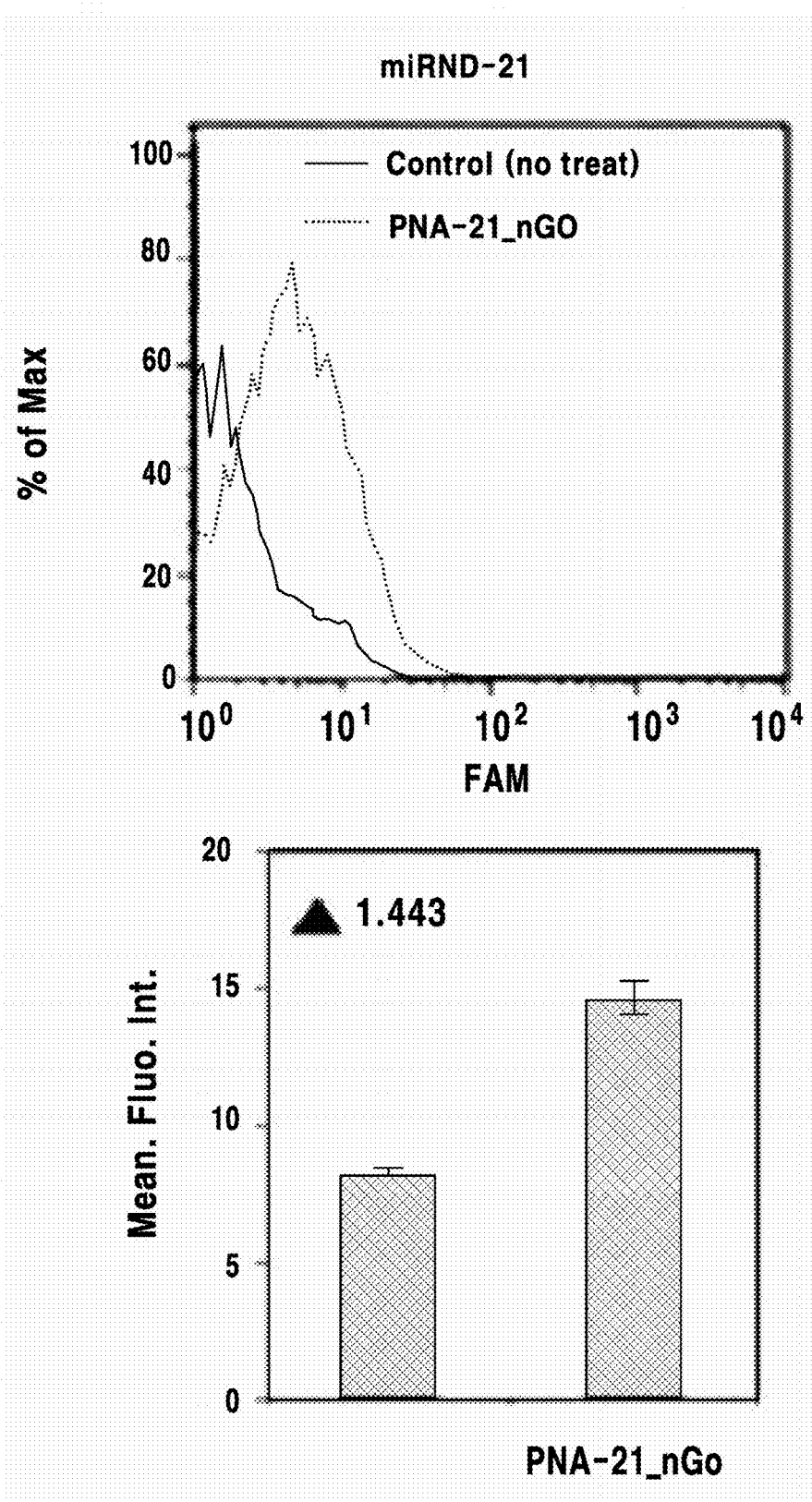
FIG. 8A shows an intracellular multi-target miRNA detection analysis result using a composition for detecting a nucleic acid in an example of the present disclosure.
Figure 8B:
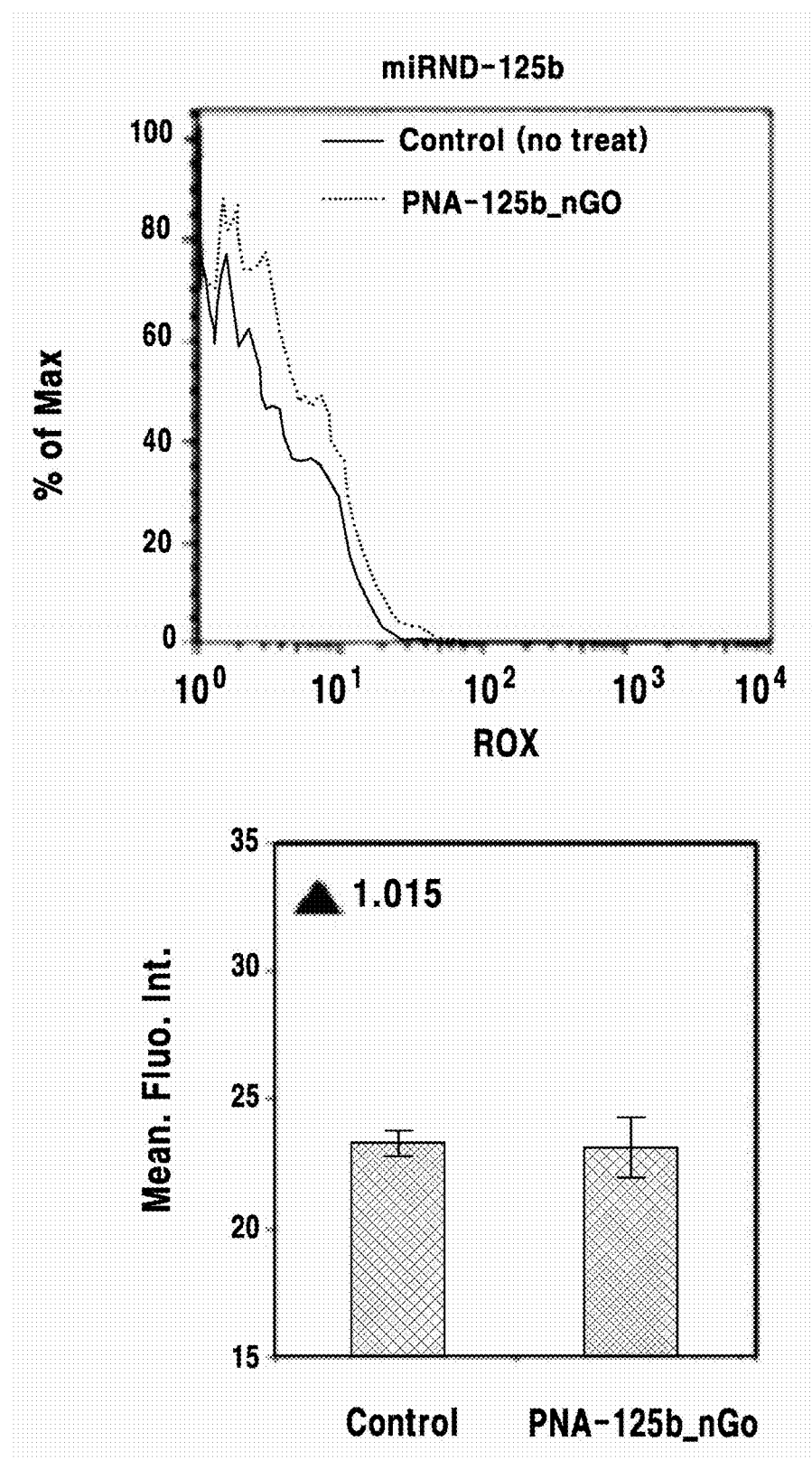
FIG. 8B shows an intracellular multi-target miRNA detection analysis result using a composition detecting a nucleic acid in an example of the present disclosure.
Figure 8C:
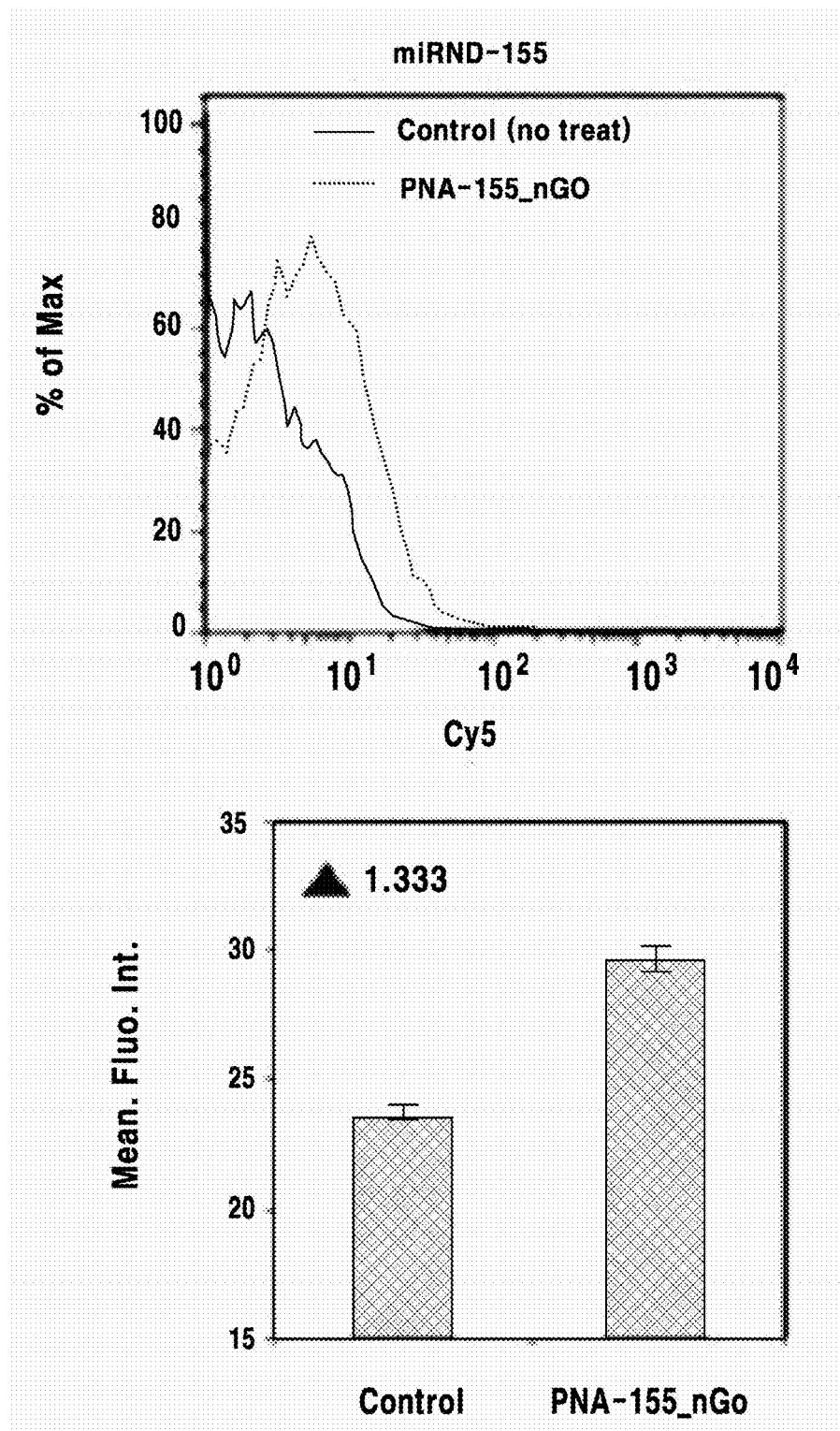
FIG. 8C shows an intracellular multi-target miRNA detection analysis result using a composition detecting a nucleic acid in an example of the present disclosure.
Figure 8D:
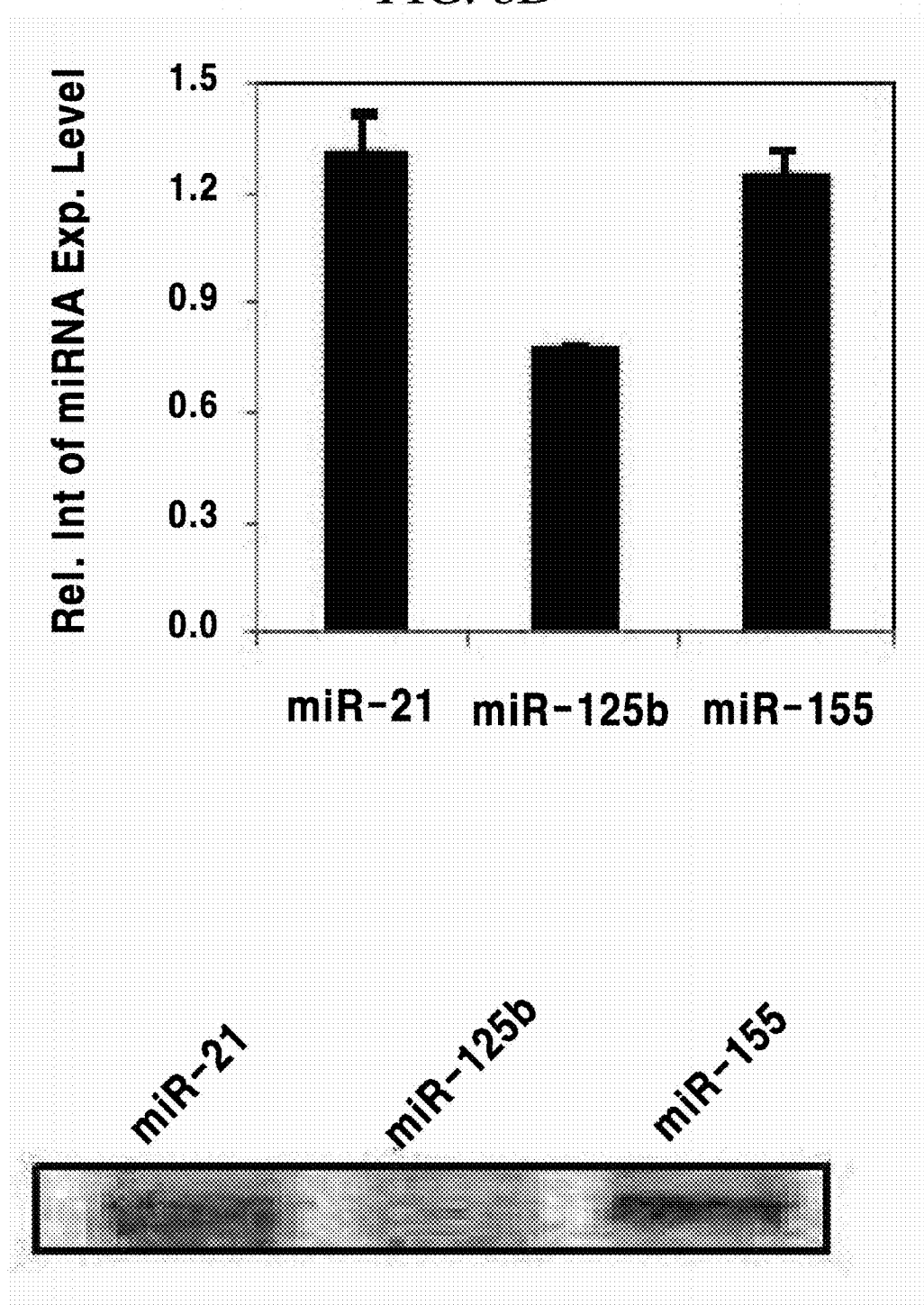
FIG. 8D shows an intracellular multi-target miRNA detection analysis result using a composition detecting a nucleic acid in an example of the present disclosure.
Figure 8E:
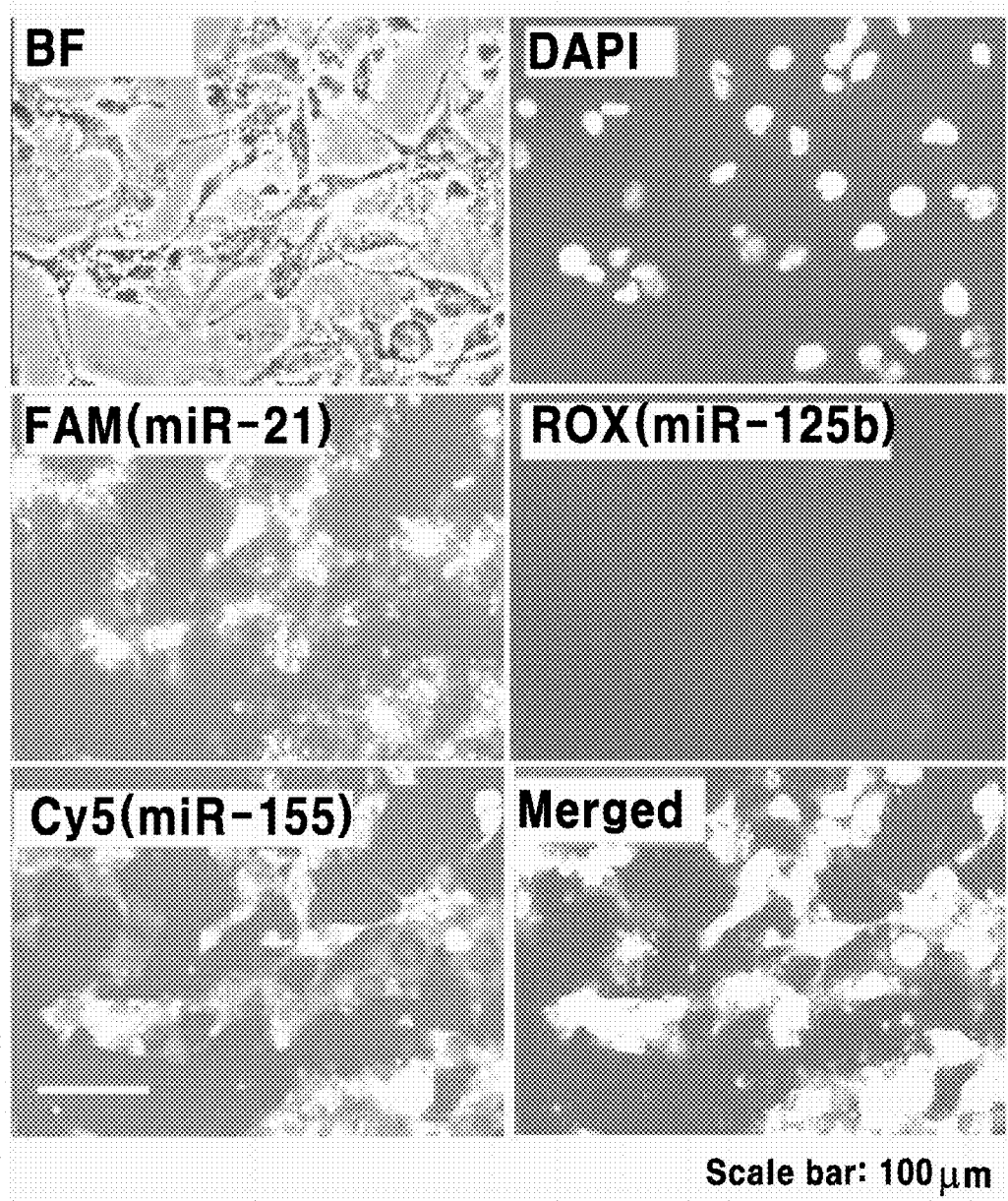
FIG. 8E shows an intracellular multi-target miRNA detection analysis result using a composition detecting a nucleic acid in an example of the present disclosure.
Figure 9A:
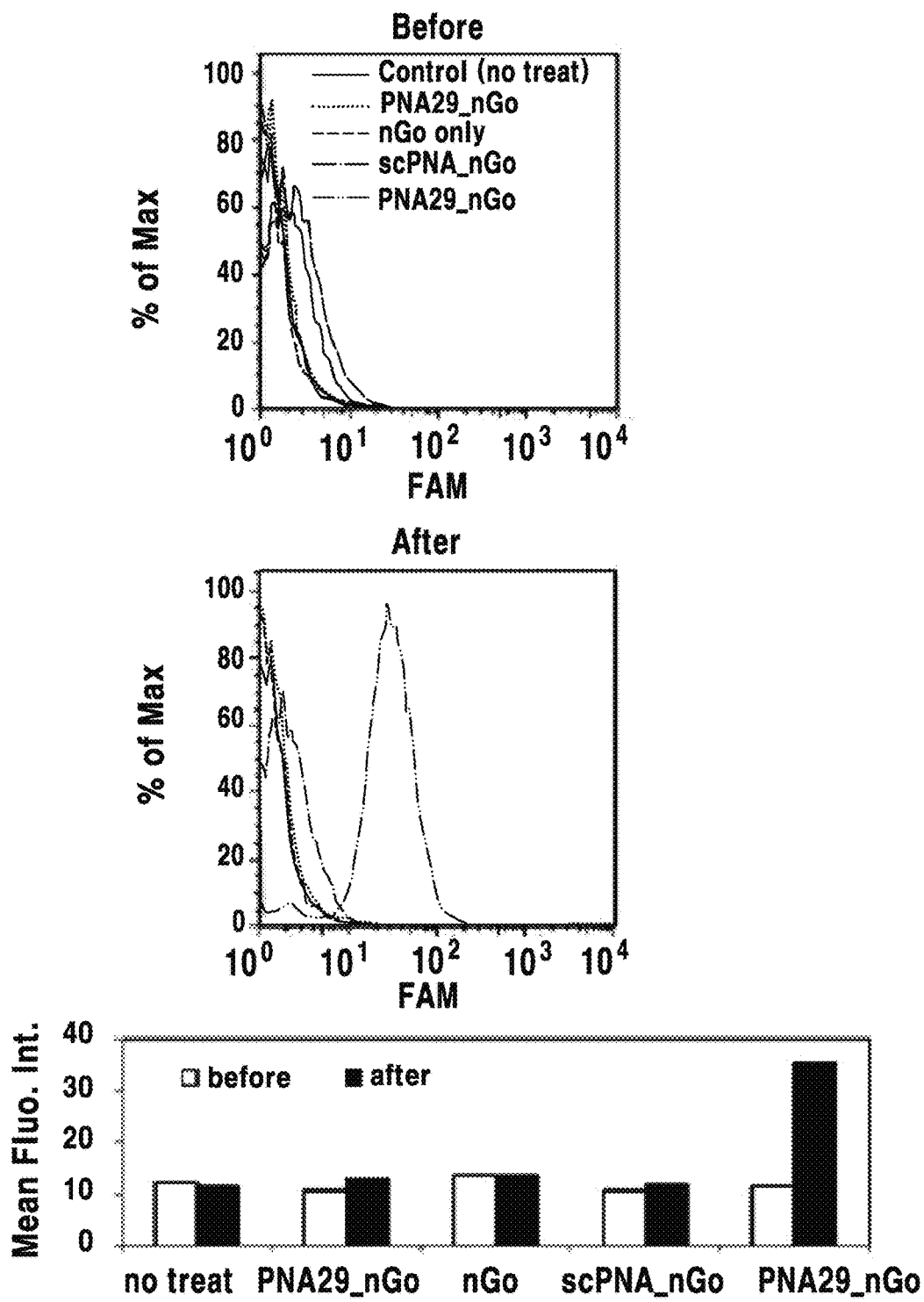
FIG. 9A shows a detection analysis result of a miRNA expression induced by doxycycline using a composition for detecting a nucleic acid in an example of the present disclosure.
Figure 9B:
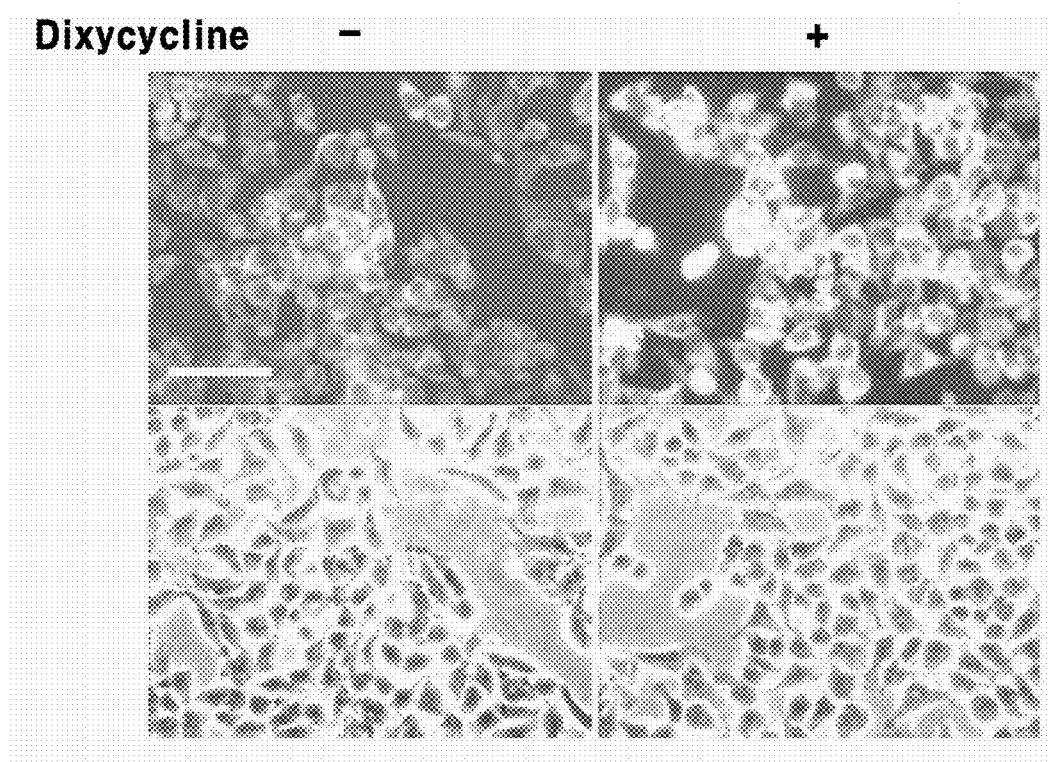
FIG. 9B shows a detection analysis result of a miRNA expression induced by doxycycline using a composition for detecting a nucleic acid in an example of the present disclosure.
Figure 9C:
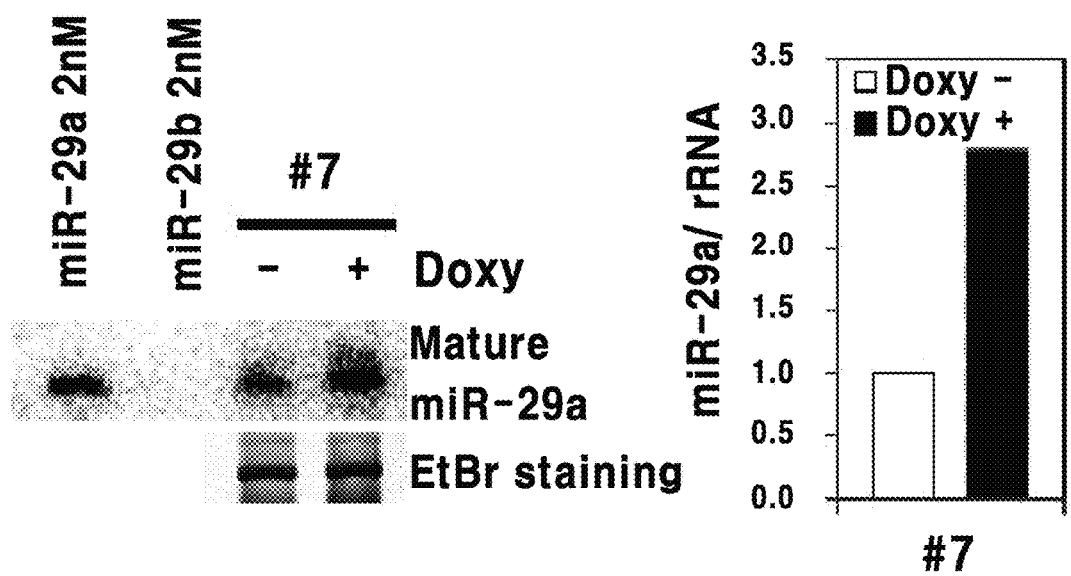
FIG. 9C shows a detection analysis result of a miRNA expression induced by doxycycline using a composition for detecting a nucleic acid in an example of the present disclosure.
Figure 9D:
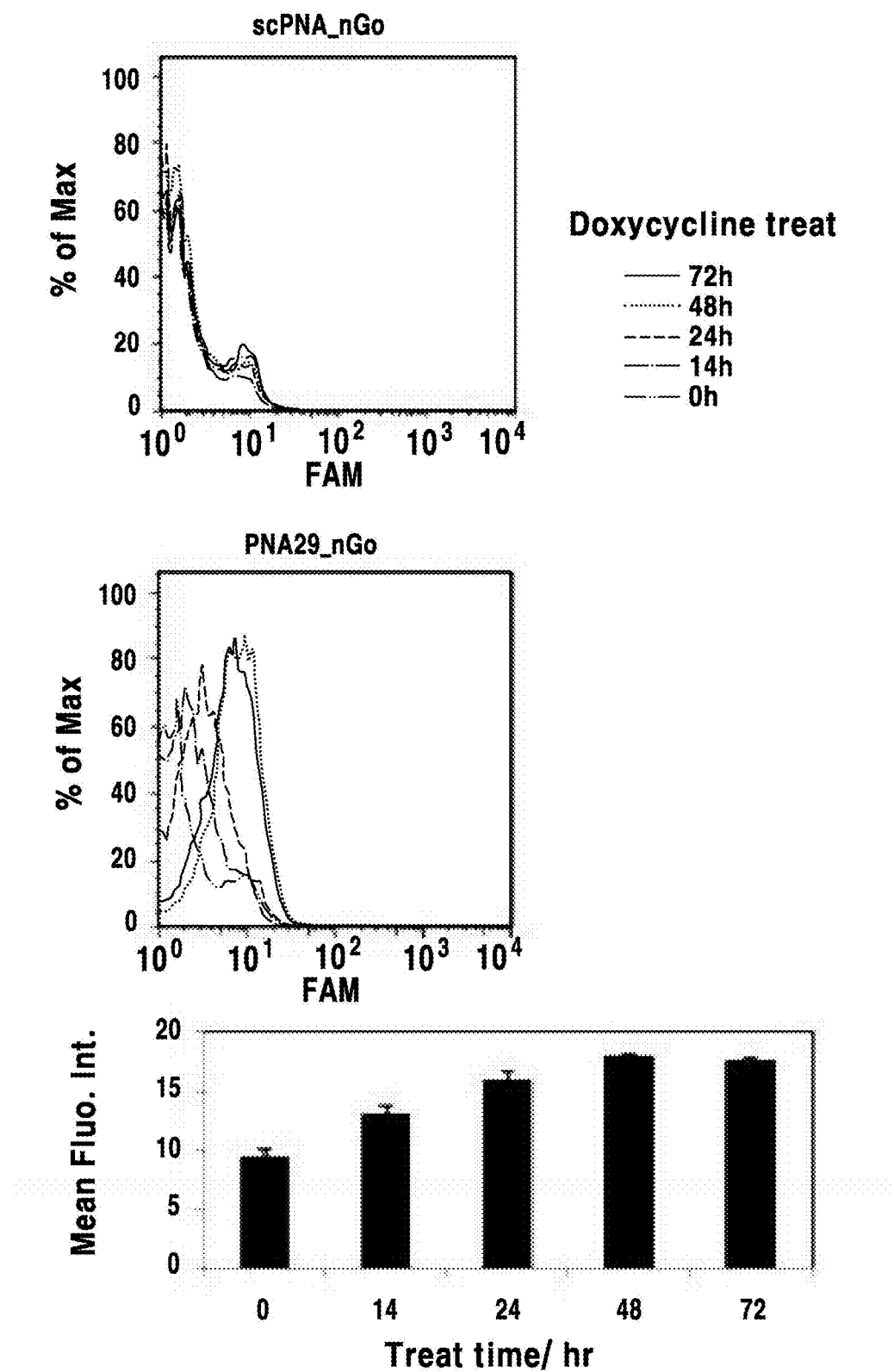
FIG. 9D provides a comparison of detection analysis results of a miRNA expression induced by doxycycline using a composition for detecting a nucleic acid in an example of the present disclosure, for respective doxycycline processing times.
Figure 9E:
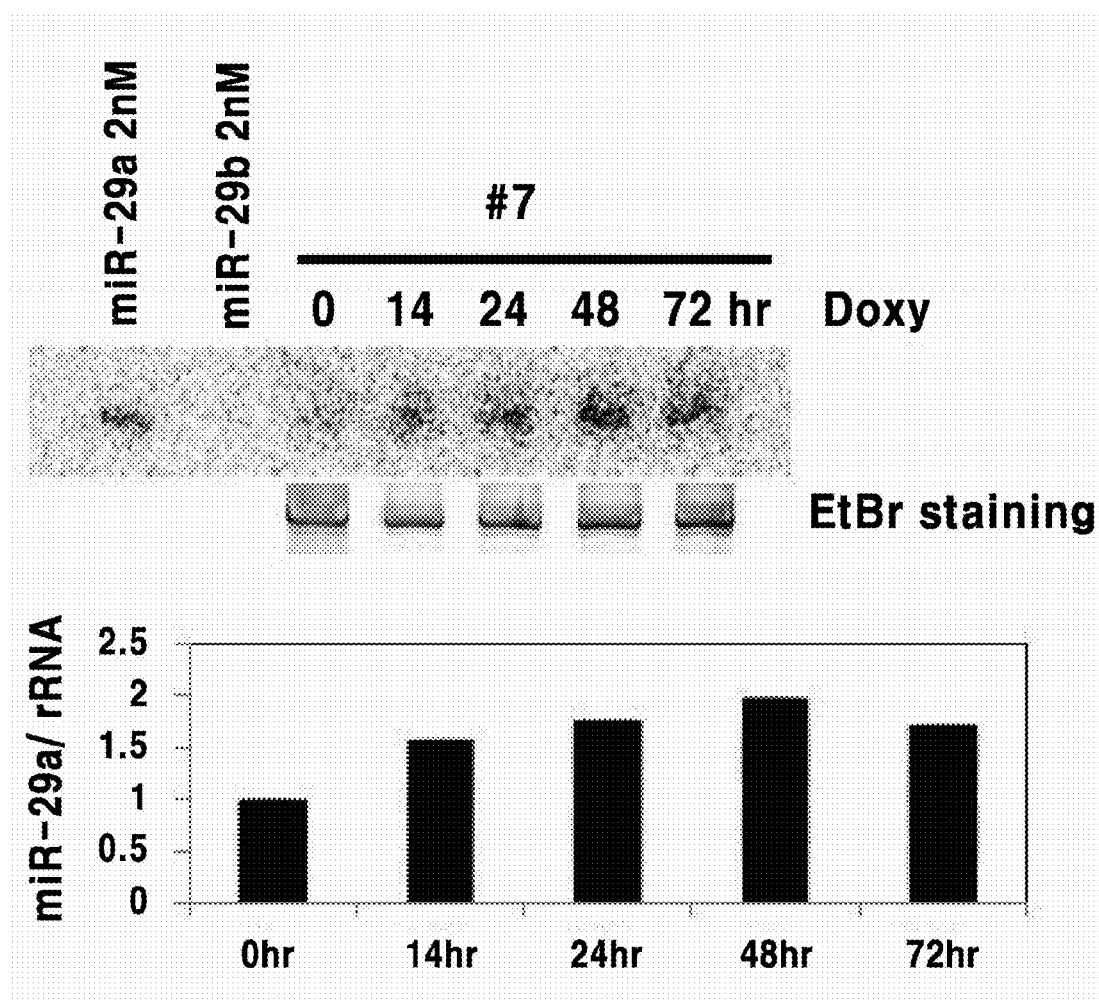
FIG. 9E provides a comparison of detection analysis results of miRNA expression induced by doxycycline using a composition for detecting a nucleic acid in an example of the present disclosure, for respective doxycycline processing times.

In this example, in order to prove that a PNA probe is combined with a miRNA as a target material in a base sequence specific manner, one to three kinds of miRNAs within a sample were accurately detected by three kinds of PNA probes and appearance of fluorescence signals was observed. First, one or more of a miRNA-21, a miRNA-125b and a miRNA-155 were included in samples in various combinations, such as one-type, two-types or three types. Then, three kinds of probes FAM-PNA-21, ROX-PNA-125b and Cy5-PNA-155 were added to the samples having various miRNA combinations and observed by using a fluorescence image analysis system. As a result, as shown in FIG. 6A to FIG. 6C, each PNA probe was found to react with only a miRNA having a complementary base sequence to that of the PNA probe and emit fluorescent light.

Example 6

Detection of a Single-Target miRNA within a Living Cell

In this example, an intracellular miRNA was detected from a living cell, and an expression amount thereof was quantified. FAM-PNA-21 was mixed with nano-size graphene oxide having a unitary quantity of 1 μg and left at a room temperature for about 10 minutes. After completing the adsorption of the FAM-PNA-21 to the graphene oxide in this way, DMEM was added to this solution so that the total volume of the solution becomes 250 μL Eighty thousand cells per a well were prepared in a 24-well cell culture plate by using a breast cancer cell lines MCF-7, MDA-MB-435 and MDA-MD-231 as a model disease cell line. Each of the prepared cell samples was treated with the above-prepared 250 μL of FAM-PNA-21 and then left for about 14 hours. Thereafter, these cells were observed by using a flow cytometer (fluorescence activated cell sorter (FACS), e.g., FACS Aria I produced by BD Co.,) and a fluorescence microscope (IX71 of Olympus Co.,) and analyzed by a semi qRT-PCR. As a result, as can be seen from FIG. 7A to FIG. 7E, a miRNA-21 present after expressed in the cell line was detected by the FAM-PNA-21 and fluorescent light was emitted. Fluorescence intensities were found to follow the sequence of expression intensity of the miRNA-21 (in the order of MCF-7, MDA-MB-231 and MDA-MB-435), as already known in the art. Further, in accordance with the present example, it was also proved that real-time detection and quantification of a target miRNA can also be performed by flow cytometry without fixing a cell.

Example 7

Detection of Multi-Target miRNs within a Living Cell

The presence of an intracellular miRNA was investigated and an expression amount thereof was quantified according to the same method as described in Example 6 excepting that only a MNA-MB-231 was used as a cell line and all of FAM-PNA-21, ROX-PNA-125b and Cy5-PNA-155 were used as PNA probes. As a result, as shown in FIG. 8A to FIG. 8D, a miRNA-21, a miRNA-125b and a miRNA-155 present after expressed in the cell line were detected by the PNA probes and fluorescent light was emitted. As for fluorescence intensities, the miRNA-21 and the miRNA-155 exhibited strong intensities, whereas the miRNA-125b showed weak intensity, the same as the expression intensities thereof as already known to those skilled in the art.

Example 8

Detection of miRNA Expressed by being Induced by Doxycycline

In this example, it was investigated, by means of flow cytometry, fluorescence microscope observation or semi qRT-PCR method, whether detection of a miRNA, which depended on presence or absence of doxycycline in a HeLa cell line genetically modified such that a miRNA-29a was expressed only under the presence of doxycycline, was accomplished. A PNA probe used in this example was PNA probe labeled with FAM. Specifically, FAM-PNA-29a having a sequence complementary to that of a miRNA-29a was used.

Expression of the miRNA-29a was observed by using the FAM-PNA-29a probe adsorbed on graphene oxide. As depicted in FIG. 9A to FIG. 9E, the miRNA-29a was detected after its expression from the HeLa cell line was induced by doxycycline, and the degree of expression changed with the time. However, in case that the probe was not used, a probe without labeled with FAM was used, only the graphene oxide was used, or a scrambled PNA (scPNA) with a scrambled sequence which was not complementary to a sequence of the miRNA-29a was used, no fluorescence was detected. That is, it was proved that a complex of a nucleic acid probe and graphene oxide emits different levels of fluorescence depending on the presence or absence of a nucleic acid as a target material when treated on a sample or a cell in which the nucleic acid as the target material having a sequence complementary to that of the probe is present.

Example 9

Figure 10:
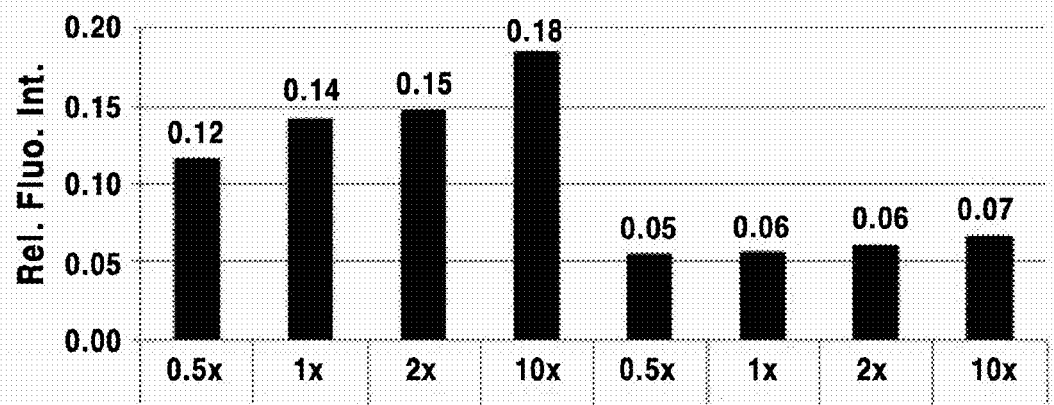
FIG. 10 is a diagram for describing a base-sequence-specific binding and a target-nucleic-acid-concentration-dependent binding of a PNA probe in an example of the present disclosure.
Figure 10:
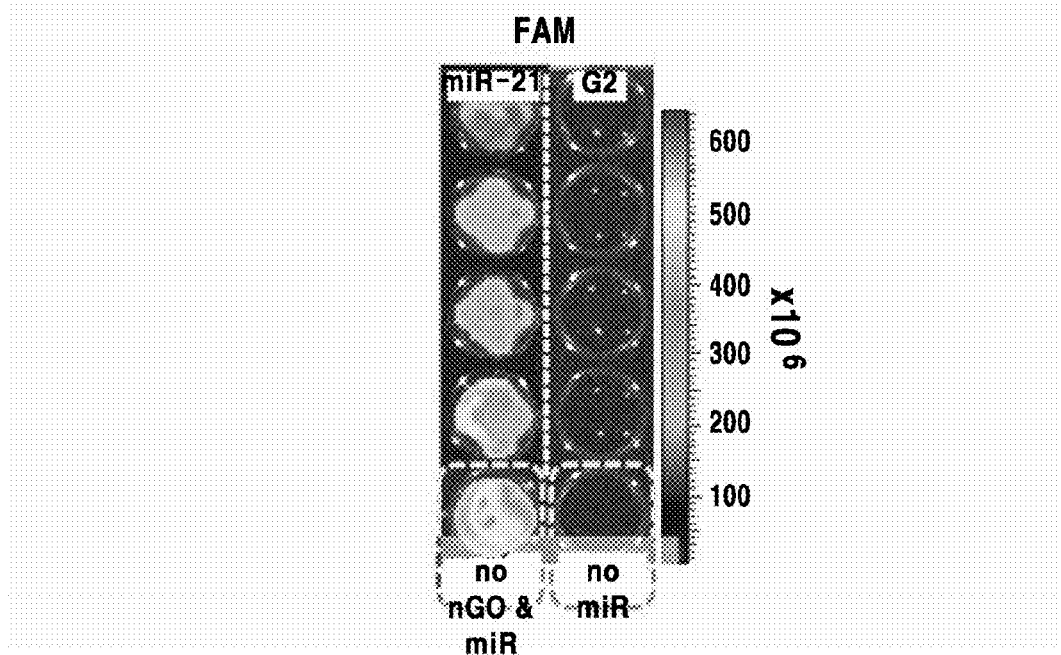

Base-Sequence-Specific PNA Probe Combination and Investigation of Fluorescence Depending on a Concentration of a Nucleic Acid as a Target Material In this example, a variation in fluorescence of a PNA probe according to a variation in a concentration of a target miRNA was observed. In this example, FAM-PNA-21 adsorbed on graphene oxide was applied to a miRNA-21 or G2 (a single-stranded RNA having a sequence of 5'-UGCG-CUCCUGGACGUAGCCU U-3' irrelevant to and different from the miRNA-21) having various concentrations. As shown in FIG. 10, the FAM-PNA-21 as the PNA probe was only combined with the miRNA-21 which was a target nucleic acid, and was separated from the graphene oxide and emitted fluorescence. The intensity of the fluorescence was found to increase in proportion to the concentration of the miRNA-21. Thus, it was proved that since the amount of the PNA probe separated from the graphene oxide increased with the rise of the concentration of the target nucleic acid, the target nucleic acid present in a sample could be detected quantitatively.

Example 10

Figure 11A:
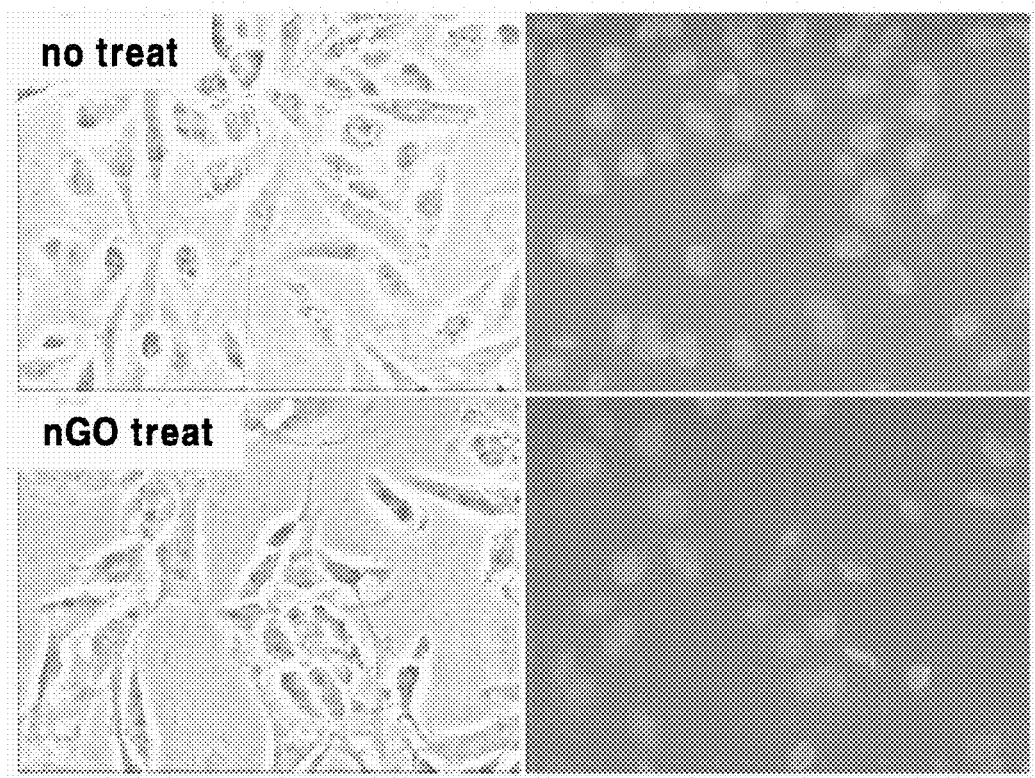
FIG. 11A shows an experimental result regarding introduction of a PNA probe into a cell which specifically reacts with the PNA probe adsorbed on graphene oxide in an example of the present disclosure.
Figure 11B:
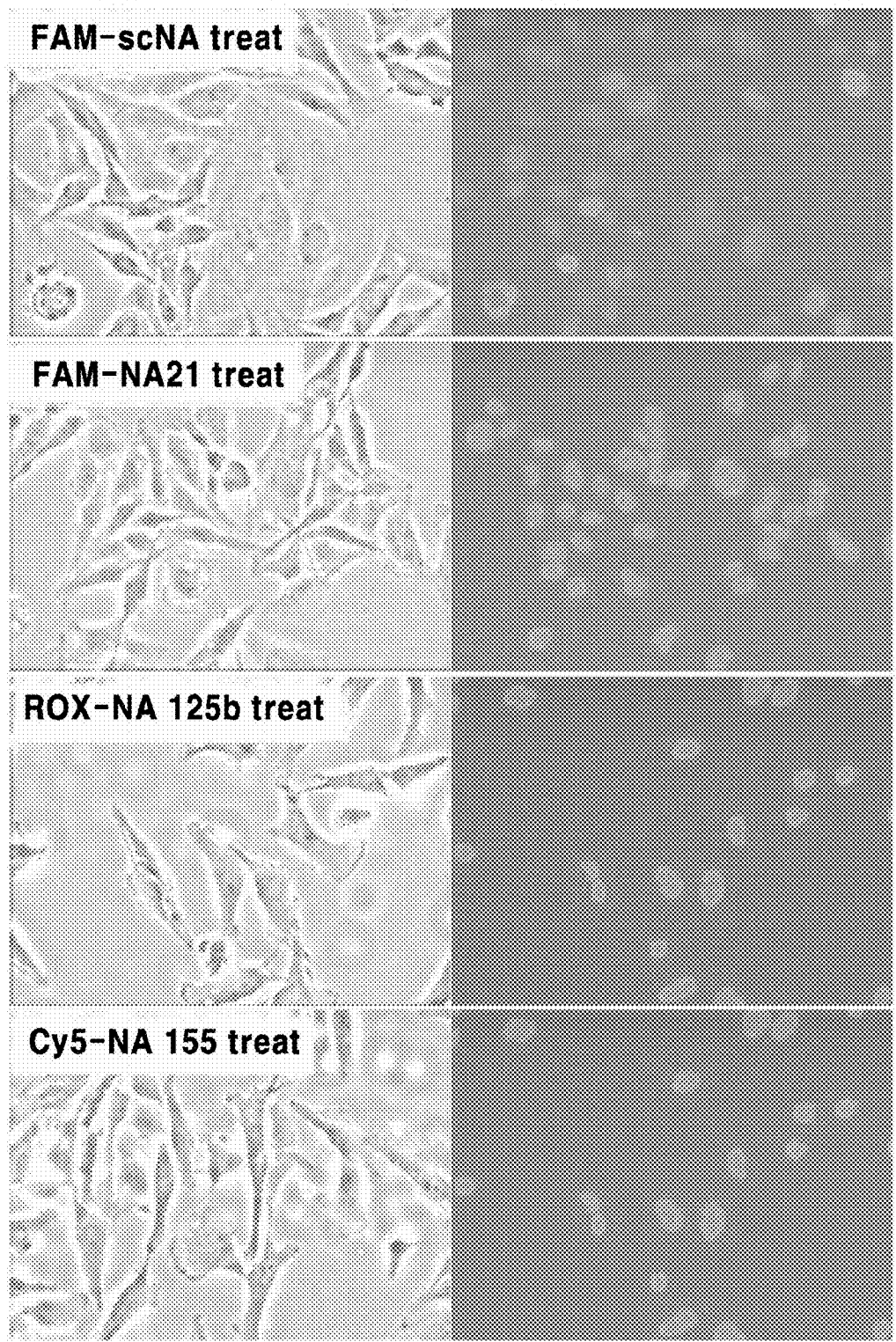
FIG. 11B shows an experimental result regarding introduction of a PNA probe into a cell which specially reacts with a PNA probe adsorbed on graphene oxide in an example of the present disclosure.

Investigation of Introduction into a Cell which Specifically Reacts to a PNA Probe Adsorbed on Graphene Oxide In this example, a cell was treated only with graphene oxide, or treated only with FAM-scPNA (a PNA probe having a scrambled sequence) as a PNA probe containing a fluorescent material which is not adsorbed on graphene oxide, FAM-PNA-21, ROX-PNA-125b or Cy5-PNA-155. Then, it was investigated whether fluorescence had occurred. As depicted in FIG. 11A and FIG. 11B, fluorescence was not observed in a non-treated cell or in a cell treated only with the graphene oxide. Further, since the PNA probe containing the fluorescence material could not be introduced to the inside of the cell in a state that the PNA probe was not adsorbed on the graphene oxide, fluorescence was also not detected even in case that only the probe was treated on the cell.

The scope of the inventive concept is defined by the following claims and their equivalents rather than by the detailed description of the example embodiments. It shall be understood that all modifications and embodiments conceived from the meaning and scope of the claims and their equivalents are included in the scope of the inventive concept.

We claim:

1. A composition for detecting a nucleic acid, comprising: at least one single stranded PNA probe adsorbed on a graphene oxide and containing a fluorescent material; wherein the nucleic acid as a target material is combined with the PNA probe so that the PNA probe is separated from the graphene oxide and a fluorescent light is emitted from the fluorescent material.

2. The composition of claim 1, wherein the nucleic acid includes a RNA or DNA.

3. The composition of claim 2, wherein the RNA includes a miRNA.

4. The composition of claim 3, wherein the miRNA includes miRNA-21, miRNA-29a, miRNA-125b, miRNA-155 or miRNA-159.

5. The composition of claim 1, wherein the PNA probe has a length of thirty bases or less.

6. The composition of claim 1, wherein the graphene oxide is in the form of a monolayer sheet.

7. The composition of claim 1, wherein the graphene oxide has a particulate form having a size in the range from 10 nm to 1 μm.

8. The composition of claim 1, wherein said at least one single stranded PNA probe includes one or more types of PNA probes containing different florescent materials respectively, and the nucleic acid as a target material includes one or more types of nucleic acids combined with the one or more types of PNA probes respectively so that multiplexed-detection of different nucleic acids is enabled.

9. The composition of claim 1, wherein said at least one single stranded PNA probe has the sequence of SEQ ID NO: 6.

10. The composition of claim 1, wherein said at least one single stranded PNA probe has at least one selected from the group consisting of SEQ ID NO: 7, SEQ ID NO: 8, SEQ ID NO: 9, and SEQ ID NO: 10.

11. The composition of claim 1, wherein said at least one single stranded PNA probe containing the fluorescent material is at least one selected from the group consisting of FAM-OO-TCAACATCAGTCTGATAAGCTA (SEQ ID NO:6), ROX-OO-TCACAAGITAGGGTCTCAGGGA (SEQ ID NO:7), Cy5-OO-CTATCACGAITAGCAITA (SEQ ID NO: 8), FAM-OO-TAGAGCTCCCTFCAATC-CAAA (SEQ ID NO:9), and FAM-OO-TAACCGATITCA-GATGGTGCTA (SEQ ID NO: 10).

* * * * *